(12) United States Patent
Ogawa

(10) Patent No.: US 8,842,288 B2
(45) Date of Patent: Sep. 23, 2014

(54) PHASE SHIFT INTERFEROMETER

(71) Applicant: Fujikura Ltd., Tokyo (JP)

(72) Inventor: Kensuke Ogawa, Sakura (JP)

(73) Assignee: Fujikura Ltd., Tokyo (JP)

( * ) Notice: Subject to any disclaimer, the term of this patent is extended or adjusted under 35 U.S.C. 154(b) by 0 days.

(21) Appl. No.: 14/037,628

(22) Filed: Sep. 26, 2013

(65) Prior Publication Data

US 2014/0029012 A1 Jan. 30, 2014

Related U.S. Application Data

(63) Continuation of application No. PCT/JP2012/054379, filed on Feb. 23, 2012.

(30) Foreign Application Priority Data

Mar. 30, 2011 (JP) ................. 2011-076744

(51) Int. Cl.
*G01B 9/02* (2006.01)
*G01N 21/47* (2006.01)
*G01M 11/00* (2006.01)

(52) U.S. Cl.
CPC .............. *G01B 9/02* (2013.01); *G01N 21/4795* (2013.01); *G01B 9/02004* (2013.01); *G01B 9/02069* (2013.01); *G01B 9/02079* (2013.01); *G01B 9/02091* (2013.01); *G01B 9/0201* (2013.01); *G01M 11/31* (2013.01)
USPC ........................................................ 356/479

(58) Field of Classification Search
CPC .... G01B 9/02; G01B 9/02004; G01B 9/0201; G01B 9/02069; G01B 9/02079; G01B 9/02091; G01M 11/31; G01N 21/4795

USPC ........................................ 356/450, 477, 479
See application file for complete search history.

(56) References Cited

U.S. PATENT DOCUMENTS 6,134,003 A * 10/2000 Tearney et al. ................ 356/479
7,426,038 B2 * 9/2008 Ogawa .......................... 356/484
(Continued)

FOREIGN PATENT DOCUMENTS

| JP | 2001-59714 A | 3/2001 |
| JP | 2009-178200 A | 8/2009 |

(Continued)

OTHER PUBLICATIONS

Horst Schreiber et al., "Phase Shifting Interferometry", Optical Shop Testing 2007, pp. 547-666, Chapter 14.

(Continued)

*Primary Examiner* — Michael A Lyons
(74) *Attorney, Agent, or Firm* — Sughrue Mion, PLLC

(57) ABSTRACT

Provided is a phase shift interferometer which comprises: a light source; an incident light path; a light circulation unit; a connection path; a light splitting/combining unit; a probe light path; a reference light path; a test sample measurement unit; a light terminal; a light-phase shifting unit which is provided in either the probe light path or the reference light path, and subjects light to phase shifting by a phase shift quantity of $\alpha_i/2$ (radian units, where $\alpha_i$ is a real number, the range of values taken by $\alpha_i$ is $0 \leq \alpha_i \leq 3\pi/2$, and i is an integer where $3 \leq i$), and periodically changes the phase shift quantity of $\alpha_i/2$; a light-emission path; a light detector which outputs an interference signal; and a controller for controlling the phase shift quantity in the light-phase shifting unit and the cycle at which the phase shift is controlled.

13 Claims, 5 Drawing Sheets

(56) References Cited

U.S. PATENT DOCUMENTS 7,948,637 B2* 5/2011 De Groot .................. 356/512
2013/0229662 A1* 9/2013 Ogawa .................... 356/453

FOREIGN PATENT DOCUMENTS

| JP | 2009-270879 A | 11/2009 |
| JP | 2011-179918 A | 9/2011 |
| WO | 2004/005974 A2 | 1/2004 |
| WO | 2012/053499 A1 | 4/2012 |

OTHER PUBLICATIONS

M. Wojtkowski et al., "Full range complex spectral optical coherence tomography technique in eye imaging", Optics Letters, Aug. 2002, pp. 1415-1417, vol. 27, No. 16.
International Search Report for PCT/JP2012/054379 dated May 29, 2012.

* cited by examiner

PHASE SHIFT INTERFEROMETER

CROSS REFERENCE TO RELATED APPLICATIONS

This application is a continuation application based on a PCT Patent Application No. PCT/JP2012/054379, filed Feb. 23, 2012, whose priority is claimed on Japanese Patent Application No. 2011-076744, filed Mar. 30, 2011, the entire contents of which are hereby incorporated by reference.

BACKGROUND OF THE INVENTION

1. Field of the Invention

The present invention relates to a phase shift interferometer used for optical measurement and tomographic image measurement based on optical coherence tomography of optical materials and optical parts.

2. Description of the Related Art

As noninvasive, high-resolution measurement means for measuring the shape of an object in an industrial field or the like, measurement using interference of light is conventionally performed using a spectral interferometer. Such a spectral interferometer is used to measure a phase of light in spectral domain.

In the spectral interferometer, propagation light emitted from a light source is split into two paths. Sample under measurement is placed in one of the paths and light transmitted through the sample is probe light. Sample is not placed in the other path and light propagating through the path in which the sample has not been placed is reference light.

The probe light and the reference light are combined to cause interference between the probe light and the reference light. Characteristics of the sample are obtained from the results of this interference.

Here, a wavelength-tunable light source which oscillates at a single wavelength is used for the light source in the spectral interferometer. Wavelength (or frequency) of the light (propagation light) emitted by the light source is swept and intensity of the interference light is measured using the wavelength (or the frequency) as a parameter. Through this measurement, a function for wavelength as a parameter is obtained, and change in phase of the light with transmission or reflection of the sample is obtained. A spectral phase can be obtained from the change in the phase of the light.

Characteristics of optical materials, optical components or the like can be evaluated by obtaining chromatic dispersion from the spectral phase obtained as described above.

Further, a spatial distribution of an optical medium in light propagation direction can be obtained by performing inverse Fourier transform of the spectral phase. From this spatial distribution, for example, a tomographic image in depth direction of the sample can be obtained.

When the spectral phase is measured from the interference light, the sign of the phase of the light cannot be determined by measuring only one of cosine (cos) component and sine (sin) component. Therefore, a mirror image of spectral phase inverted around the origin of the frequency axis against the spectral phase which should be obtained in reality is obtained. As a result, it cannot be determined whether the chromatic dispersion increases or decreases or whether the distance in the depth direction increases or decreases.

Therefore, to avoid the generation of the mirror image spectrum on the frequency axis as described above is, it is important to measure both of the cos component and the sin component, namely, two orthogonal components such that the sign of the phase of the light can be determined.

An interferometer capable of measuring two orthogonal components described above includes a phase shift interferometer. A configuration of a general phase shift interferometer is disclosed in "Phase shifting interferometry" in "Optical Shop Testing," by H. Schreiber, J. H. Bruning and J. E. Greivenkamp, edited by D. Malacara (3d ed.) chap. 14, pp. 547-666 (J. Wiley & Sons, New Jersey, 2007), which is hereinafter referred to as Non-Patent Document 1. In the phase shift interferometer described in Non-Patent Document 1, a phase shifter may be provided in one of two paths constituting the phase shift interferometer. Phase shift generated in this phase shifter is switched to "0" and "π/2" (in radians), and two orthogonal components of the cos component and the sin component are measured.

Further, in Non-Patent Document 1, a PZT (lead titanate zirconate: piezoelectric material) transducer is mounted as the phase shifter on a mounting portion of a mirror or a lens. As the PZT (lead titanate zirconate: piezoelectric material) transducer is mounted on the mounting portion of the mirror or the lens, the mirror or the lens is displaced to switch a phase shift amount for light propagating through a path on one side.

Furthermore, a plurality of algorithms for obtaining, when a non-interference component that is a background component is included in a measured interference waveform, two orthogonal components by removing this non-interference component from the interference waveform to extract the interference component are described in Non-Patent Document 1.

Further, there is an example in which a method of switching a phase shift amount shown in the phase shift interferometer and measuring two orthogonal components is applied to a spectrum interferometer. For example, Japanese Unexamined Patent Application, First Publication No. 2001-059714, which is hereinafter referred to as Patent Document 1 discloses measurement of two orthogonal components of a spectral phase using a wavelength scanning phase shift interferometer. The wavelength-swept phase shift interferometer described in Patent Document 1 is configured as described below.

A light beam emitted from a light source including an external cavity LD (Laser Diode: semiconductor laser) is converted to collimated light by a telescope, and this collimated light is emitted to a Michelson interferometer.

In the Michelson interferometer, the incident collimated light is split into irradiation light and reference light, the irradiation light is radiated to an object under measurement and the reference light is radiated to a PZT mirror functioning as a phase shifter. The irradiation light radiated to the measured object is reflected from a surface of the measured object and converted to object light.

Also, the reference light reflected from the PZT mirror and the object light emitted by the measured object are reflected by a beam splitter, transmitted through a polarizer and then superimposed on a photoelectric surface of a CCD (Charge Coupled Device) in a CCD camera. Through this superposition, an interference signal of the reference light and the object light is detected on the photoelectric surface.

The PZT mirror is controlled to be in a position corresponding to arbitrary phase and an interference spectrum is measured in such a phase. Also, after the measurement of the interference spectrum at the phase is completed, the PZT mirror is controlled to be in a position corresponding to a phase different from the above phase, and measurement of the interference spectrum is performed at this phase.

The interference spectra in different phase components are measured for each phase component by repeatedly performing a process of changing the position of the PZT mirror and measuring the interference spectrum in different phases as described above. Here, determination of the phase value is performed only in the center wavelength in a wavelength range in one sweep when the wavelength is swept, and a phase value in other wavelengths in the same wavelength range is considered to be equal to the phase value in the center wavelength.

Further, when a tomographic image in optical coherence tomography is obtained using the phase shift spectral interferometer, mirror image data in the tomographic image can also be eliminated (e.g., see "Full range complex spectral optical coherence tomography technique in eye imaging," by M. Wojtkowski, A. Kowalczyk, R. Leitgeb and A. F. Fercher, OPTICS LETTERS vol. 27, no. 16, pp. 1415-1417 (2002), which is hereinafter referred to as Non-Patent Document 2).

Further, two orthogonal components can be obtained using a heterodyne optical spectrum analyzer having a configuration of an optical beam splitter which emits interference components corresponding to different phase components in parallel from three respective output ports instead of using the phase shifter (e.g., see PCT International Publication No. WO 2004/005974, which is hereinafter referred to as Patent Document 2). Simultaneously obtaining two orthogonal components in heterodyne interference through a parallel process using interference components emitted in parallel from three output ports is described in Patent Document 2.

However, in the swept-wavelength phase shift interferometer disclosed in Patent Document 1, approximation is performed so that swept wavelength is equal to the center wavelength. Therefore, a configuration based on a scheme of obtaining the predetermined phase values only in the center wavelength, with at least three predetermined phase values in the central wavelength corresponding to phase values in other scanning wavelengths, is disclosed in Patent Document 1.

In a scheme of Patent Document 1, the chromatic dispersion with the propagation of the path in the interferometer and the reflection from a measured object is small enough not to affect measurement accuracy and can be neglected, and a correct function is performed under a condition that an approximation that the phase of the propagation light linearly changes with respect to the frequency is satisfied.

On the other hand, when the chromatic dispersion cannot be neglected relative to measurement accuracy, only low-precision measurement can be performed, and when the chromatic dispersion of the measured object is characteristics to be measured, the phase does not linearly change with the frequency and therefore the chromatic dispersion cannot be precisely measured.

In other words, when the measurement of the chromatic dispersion is intended, the interferometer having the configuration disclosed in Patent Document 1 cannot be used because of measurement conditions of such a scheme.

Further, the interferometer disclosed in Patent Document 1 is constructed with a free-space optical system defining an interference path to cause interference of light in air as can be seen from the configuration illustrated in FIG. 1 of Patent Document 1, which is an obstacle to downsizing an apparatus.

Here, when an interference path is configured of an optical fiber for the purpose of downsizing and easy configuration, it may be considered that the phase does not linearly change with the frequency because of chromatic dispersion in the optical fiber, and measurement accuracy of the chromatic dispersion of a measured object is degraded.

Therefore, it is necessary for the chromatic dispersion in the optical fiber to be suppressed so as not to affect the measurement accuracy by shortening the length of the optical fiber.

However, if the optical fiber is shortened so as not to affect the measurement accuracy, the length of the optical fiber to reach a diagnosis part in optical coherence tomography cannot be secured.

Further, it is necessary for a wavelength sweep range (a wavelength bandwidth in which a wavelength is swept, i.e., a wavelength range for measurement) to be narrowed to a range in which approximation of the phase linearity to the frequency is possible. Since the wavelength sweep range is narrowed in this way, only an interference signal in a narrow range is obtained and resolution of the tomographic image is degraded.

Furthermore, in the interferometer disclosed in Patent Document 1, a PZT mirror is used to constitute the phase shifter, the PZT mirror is fixed to a position corresponding to each of predetermined phase values, and wavelength sweep is repeatedly performed to measure an interference spectrum in each phase value.

Also, the two orthogonal components of interference based on a plurality of phase values are obtained by measuring the interference spectrum in the plurality of phase values by repeatedly performing this sweep.

When the scheme of obtaining the two orthogonal components of Patent Document 1 is applied to an interferometer using optical fibers, position of the PZT mirror is changed due to change in optical path length of the optical fiber with temperature change, and the phase in the interferometers varies while the interference spectrum in a plurality of phase values are being acquired. Therefore, a phase value set for the interferometer differs from a phase value with which measurement is actually performed.

As a result, since orthogonality of the two orthogonal components is impaired, a ripple is generated in chromatic dispersion data or a tomographic image. Measurement accuracy of the chromatic dispersion is greatly degraded due to this ripple such that evaluation is impossible or the tomographic image is disturbed and diagnosis based on the tomographic image cannot be performed.

Similarly, the interferometer disclosed in Non-Patent Document 2 also suffers from the same problems as Patent Document 1 since the PZT minor is moved to change the phase shift amount.

On the other hand, the interferometer described in Patent Document 2 has a configuration of an optical beam splitter that emits interference components corresponding to different phase components from three output ports in parallel. Therefore, since it is unnecessary to use the phase shifter and it is possible to measure interference components of respective different phase components simultaneously, there are no effects of the phase variation as in Patent Document 1.

However, it is necessary to provide a photodetector for each of three output ports. As a result, the number of photodetectors increases, the configuration of the interferometer becomes more complicated as the number of photodetectors increases, it is difficult to reduce the size of the interferometer, and manufacturing cost increases.

SUMMARY

The present invention provides a phase shift interferometer (phase shift fiber spectrum interferometer) which has higher measurement accuracy as compared to a conventional one, has a simple configuration, is easily reduced in size and inexpensive, and which is capable of being used to measure chromatic dispersion and tomographic photography in optical coherence tomography.

According to a first aspect of the present invention, a phase shift interferometer may include: a light source that includes a first emission end, wavelength-swept single longitudinal mode light to generate propagation light, and emits the propagation light from the first emission end; an incidence optical path that includes one end connected to the first emission end, the incidence optical path including a single mode optical fiber having a polarization-maintaining characteristic, which propagates the propagation light; an optical circulation unit that includes a first incidence end, a first incidence and emission end, and a second emission end, the first incidence end being connected to the other end of the incidence optical path, and the propagation light incident from the first incidence end being emitted from the first incidence and emission end or combination light incident from the first incidence and emission end being emitted from the second emission end; a connection path that includes one end connected to the first incidence and emission end, the connection path including a single mode optical fiber having polarization-maintaining property; an optical beam splitting and combining unit having a second incidence and emission end, a third incidence and emission end, and a fourth incidence and emission end, the second incidence and emission end being connected to the other end of the connection path, and the light branch and combination unit splitting the propagation light incident from the second incidence and emission end into first propagation light and second propagation light having the same polarization as the first propagation light, emitting the first propagation light from the third incidence and emission end, emitting the second propagation light from the fourth incidence and emission end, combining first reflected propagation light incident from the third incidence and emission end with a second reflected propagation light incident from the fourth incidence and emission end to generate the combination light that is an interference result, and emitting the combination light from the second incidence and emission end; a probe optical path having one end connected to the third incidence and emission end, the probe optical path including a single mode optical fiber having a polarization-maintaining property; a reference optical path having one end connected to the fourth incidence and emission end, the reference optical path including a single mode optical fiber having a polarization-maintaining property; a sample measurement unit that includes a fifth incidence and emission end, the fifth incidence and emission end being connected to the other end of the probe optical path, and the sample measurement unit reflecting the first propagation light incident from the fifth incidence and emission end, from a sample surface of a measurement target arranged therein to generate the first reflected propagation light, and emitting the first reflected propagation light from the fifth incidence and emission end; an optical termination portion that includes a sixth incidence and emission end and a reflection surface, the sixth incidence and emission end being connected to the other end of the reference optical path, and the optical termination portion totally reflecting the second propagation light incident from the sixth incidence and emission end in the reflection surface to generate the second reflected propagation light, and emitting the second reflected propagation light from the sixth incidence and emission end; an optical phase shift unit that is provided in one of the probe optical path and the reference optical path and performs phase shift of the light propagating through the one optical path by a phase shift amount $\alpha_i/2$ (in radians; $\alpha_i$ is a real number, $0 \leq \alpha_i \leq 3\pi/2$, i is an integer, and $\alpha_i$, $3 \leq i$), and periodically changes the phase shift amount $\alpha_i/2$; an emission optical path that includes one end connected to the second emission end, the emission optical path including a single mode optical fiber to propagate the combination light; an optical detection unit that includes a second incidence end, the other end of the emission optical path being connected to the second incidence end, and an optical detection unit converting the combination light incident from the second incidence end into an electrical signal to generate an interference signal and outputting the interference signal; a control unit that controls a period for controlling the phase shift amount and the phase shift in the optical phase shift unit whenever the wavelength sweep is performed in synchronization with the wavelength sweep of the propagation light in the light source, and generates a sampling signal for acquiring the interference signal corresponding to an $i^{th}$ light component in time series in order in which i increases within one period of the phase shift; and a data acquisition unit that acquires the interference signal corresponding to the $i^{th}$ light component in time series whenever the sampling signal is supplied.

According to a second aspect of the present invention, in the phase shift interferometer according to the first aspect, a range of values that i can have may be m, and the control unit may perform an interpolation process in which a measurement interval of each wavelength component is 1/m, on each of the $i^{th}$ light components, such that the number of data points of all interference signals increases by a factor of m.

According to a third aspect of the present invention, in the phase shift interferometer according to the first aspect or the second aspect, a total number of $\alpha_i$ elements may be equal to or more than 3 (i≥3), and the control unit may extract, from the elements, a first light component of a phase $\alpha_1$, a second light component of a phase $\alpha_2$ and a third light component of a phase $\alpha_3$ as three elements, and acquire the interference signal from each of the first light component, the second light component and the third light component.

According to a fourth aspect of the present invention, in the phase shift interferometer according to the third aspect, the total number of $\alpha_i$ elements may be equal to or more than 30 (i≥30).

According to a fifth aspect of the present invention, the phase shift interferometer according to any one of the first to fourth aspects may further include: an optical delay unit provided in one of the probe optical path and the reference optical path to adjust an optical path length difference between the probe optical path and the reference optical path.

According to a sixth aspect of the present invention, in the phase shift interferometer according to the fifth aspect, the optical delay unit may be provided in the one of the probe optical path and the reference optical path, and the optical phase shifter may be provided in the other of the probe optical path and the reference optical path.

According to a seventh aspect of the present invention, in the phase shift interferometer according to the fifth aspect, the optical delay unit and the optical phase shifter are integrally provided in one of the probe optical path and the reference optical path.

According to an eighth aspect of the present invention, in the phase shift interferometer according to any one of the third to seventh aspects, the control unit may include: a first reception unit that receives the interference signal of the first light component; a second reception unit that receives the interference signal of the second light component; and a third reception unit that receives the interference signal of the third light component.

According to a ninth aspect of the present invention, in the phase shift interferometer according to any one of the third to seventh aspects, the data acquisition unit may acquire, as a measurement unit, the first light component, the second light component and the third light component as a data set in time series with each sweep of the wavelength.

According to a tenth aspect of the present invention, in the phase shift interferometer according to any one of the first to ninth aspects, the sample measurement unit may include: a first internal path that includes one end connected to the fifth incidence and emission end and the other end connected to an incidence end of the sample that is the measurement target, the first internal path including a single mode optical fiber having a polarization-maintaining characteristic; and a second internal path that includes one end connected to an emission end of the sample, and the other end having a total reflection mirror provided therein, the second internal path including a single mode optical fiber having a polarization-maintaining characteristic.

According to a eleventh aspect of the present invention, in the phase shift interferometer according to any one of the first to ninth aspects, the sample measurement unit may include: an internal path that includes one end connected to the fifth incidence and emission end and the other end from which parallel light is emitted, the internal path including a single mode optical fiber having a polarization-maintaining characteristic; and a lens that condenses the parallel light emitted from the other end of the internal path and radiates the resultant parallel light on the surface of the sample that is the measurement target, and wherein reflected parallel light reflected from the surface of the sample and then incident from the other end of the internal path may be emitted from the fifth incidence and emission end as the second reflected propagation light.

According to a twelfth aspect of the present invention, in the phase shift interferometer according to any one of the first to eleventh aspects, the data acquisition unit may convert the spectral phase acquired as a function of a wavelength to a function of a frequency, obtain a dispersion parameter from a spectral phase difference between adjacent frequencies, and obtain chromatic dispersion from the dispersion parameter.

According to a thirteenth aspect of the present invention, in the phase shift interferometer according to any one of the first to eleventh aspects, the data acquisition unit has an optical coherence tomography function of converting the spectral phase acquired as a function of a wavelength into a function of a frequency, performing an inverse Fourier transform of the spectral phase, and indicating an inverse Fourier transform of the spectral phase as a function of a propagation distance of the propagation light.

According to an aspect of the present invention, since the phase shift interferometer is configured of a probe optical path and a reference optical path of optical fibers having a polarization-maintaining property instead of using a space optical system, the configuration of an apparatus is simple, it is unnecessary to arrange parts for the space optical system, and it is possible to reduce the size of the apparatus in comparison with configurations of the related art.

Further, according to an aspect of the present invention, it is possible to extract the interference elements from the $i^{th}$ light component having different phase shift amounts from the first reflected propagation light and the second reflected propagation light in the same stable polarization state and to perform the measurement of the chromatic dispersion of a light pulse and tomographic photography in optical coherence tomography with high precision and high sensitivity as compared to a conventional case by periodically switching the phase difference of the second propagation light and the second reflected propagation light propagating through the reference optical path relative to the first propagation light and the first reflected propagation light propagating through the probe optical path in time series from 0 to $3\pi/2$ radians, in the probe optical path and the reference optical path constituting the interferometer which cause the propagation light to propagate through the interferometer in a state in which polarization of the propagation light is maintained using the optical fiber having a polarization-maintaining property.

DETAILED DESCRIPTION OF THE PREFERRED EMBODIMENT

Figure 1:
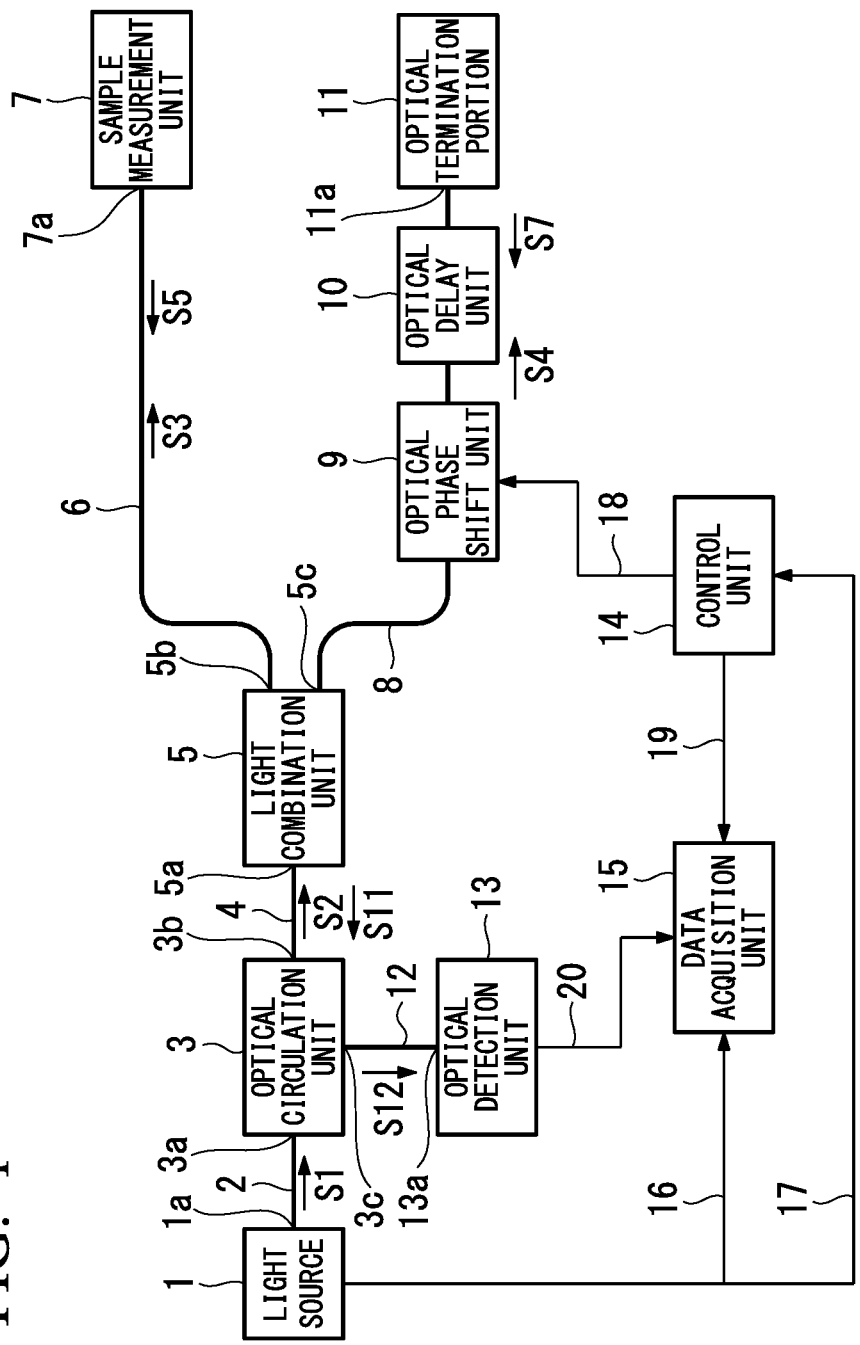
FIG. 1 is a block diagram illustrating a configuration example of a phase shift interferometer in accordance with a first preferred embodiment of the present invention.

Hereinafter, preferred embodiments of the present invention will be described with reference to the accompanying drawings. Further, the preferred embodiment is, for example, a preferred embodiment of a phase shift interferometer (phase shift fiber spectrum interferometer) available for measurement of chromatic dispersion when a measured object is an optical fiber or an optical part or tomographic photography in optical coherence tomography.

First, a method of removing a non-interference component from an interference spectrum, which is used in the phase shift interferometer in the preferred embodiment, will be described.

(Removal of Non-Interference Component Overlapping Interference Component from Interference Spectrum)

In the case of an interferometer using a space optical system, a flat beam splitter is used to branch incident light toward two propagation paths (paths for probe light and reference light which will be described below) of the phase shift interferometer. On the other hand, in the case of an interferometer using optical fibers, an optical splitter including the optical fiber or a light guide is used to branch incident light toward two propagation paths of the phase shift interferometer.

When incident light is branched toward the two propagation paths of the phase shift interferometer, the branch ratio of the incident light in the two propagation paths is ideally 50:50. However, in fact, the branch ratio of the incident light in the two propagation paths is not necessarily 50:50 since an error is generated at the time of designing and manufacturing the optical splitter or the like.

Further, when a wide spectrum area such as a C band or an L band in a wavelength band used in optical communication is a target, it is theoretically difficult to maintain the branch ratio of the incident light in the two propagation paths at 50:50 in association with light having each wavelength. Therefore, the branch ratio (and a combination ratio from two interferometers) to the two interference paths deviates from 50:50.

If the branch ratio and the combination ratio deviate from 50:50 due to the factors described above, a non-interference component that is a background component (background) overlaps an interference component in the interference spectrum to be measured. Therefore, it is necessary to remove the non-interference component from the interference spectrum in order to obtain two orthogonal components of an interference fringe.

Therefore, it is necessary to always maintain the branch ratio and the combination ratio at 50:50 for different wavelengths in order to maintain a state in which there is no non-interference component. Therefore, in consideration of wavelength dependence of all elements constituting a spectrum shearing interferometer, it is necessary to design a spectrum shearing interferometer which has a very unique configuration.

Further, a stabilization mechanism for suppressing a change in path length of the spectrum shearing interferometer due to thermal expansion of a constituent element and a variation of a refractive index of the constituent element due to a thermo-optic effect by maintaining a constant temperature is necessary in order to prevent variation (fluctuation) of the branch ratio and the combination ratio.

However, in the spectrum shearing interferometer having such a unique configuration, constituent elements are complicated and the number of elements is increased. Therefore, an apparatus is large and is not desirable for practical use.

Here, the non-interference component that is a background component and degrades precision of chromatic dispersion characteristics can be removed through a mathematical operation using three phase components.

For three or more phase shifts having different values, an interference fringe which the non-interference component which is a background component overlaps is measured. As the measurement of the interference fringe is performed, the non-interference component can be removed through a mathematical operation and a change in the spectral phase can be obtained from two orthogonal components. Use of this method makes it unnecessary to maintain both of the branch ratio and the combination ratio at 50:50 or to introduce the stabilization mechanism for suppressing the variation due to temperature, and it is possible to reduce the size of the spectrum shearing interferometer and manufacture the spectrum shearing interferometer simply.

A procedure of the process of measuring the interference fringe that the non-interference component overlaps for phase shifts having three different phase shift values and deriving the change in the spectral phase from the two orthogonal components as described above will be described below. Further, when different phase shifts having four or more phase shift values are used, the non-interference component which is a background component can be removed and the change of the spectral phase can be obtained with high precision through the same procedure as the procedure of the process using the phase shifts having three values to be described below.

Hereinafter, a procedure of removing the non-interference component from the interference spectrum using interference components having three different phase shift values will be described based on equations.

In the following description, three phase components having different phase shifts are assumed to be a 0 component (a component when the phase is 0), a $\pi$ component (a component when the phase is $\pi$), and an $\alpha$ component (a component when the phase is $\alpha$). Here, $\alpha$ is any real number value greater than 0 and smaller than $\pi$ ($0<\alpha<\pi$) (in the preferred embodiment, units of the phase shift are assumed to be radians).

Further, the interference spectrum in the phase shifts of 0, $\pi$, and $\alpha$ described above includes an interference component and a non-interference component which is a background component overlapping this interference component, and is expressed as shown in Equation (1) below using a matrix type equation.

$$\begin{pmatrix} I_0(\lambda) \\ I_\pi(\lambda) \\ I_\alpha(\lambda) \end{pmatrix} = \begin{pmatrix} I_{back}(\lambda) + I_{int}(\lambda)\cos[\phi(\lambda)] \\ I_{back}(\lambda) + I_{int}(\lambda)\cos[\phi(\lambda) + \pi] \\ I_{back}(\lambda) + I_{int}(\lambda)\cos[\phi(\lambda) + \alpha] \end{pmatrix} \quad (1)$$

On the left side of Equation (1) above, there are interference spectra, which the non-interference component overlaps, in the respective phase shifts 0, $\pi$ and $\alpha$, from top to bottom. Further, in a matrix of a right side, $\phi(\lambda)$ is a spectral phase. When the phase shift is changed periodically continuously in the measurement, the value of the interference signal is sequentially repeatedly measured with three values of phase shifts 0, $\pi$ and $\alpha$ to obtain the interference spectrum in the respective phase components. For example, the phase shift is alternately switched in order of 0, $\pi$ and $\alpha$. Specifically, $0 \to \alpha \to \pi \to 0 \to \alpha \to \pi \ldots$ and $0 \to \alpha \to \pi$ is one period for repetition.

Further, on the right side of Equation (1) above, a first term ($I_{back}(\lambda)$) denotes a non-interference component which is each background component, and a second term ($I_{int}(\lambda)\cos[\ldots]$) denotes an interference component. This non-interference component does not depend on the phase shift but depends on only the wavelength $\lambda$ of a light pulse. In each interference component, a value of each phase shift is included in a variable part of the cos function.

Further, in the preferred embodiment, a phase shift interferometer in reflection arrangement for splitting propagation light into a first propagation light and a second propagation light, causing the first propagation light and the second propagation light to propagate through two propagation paths (interference paths), and measuring an interference spectrum of a first reflected propagation light obtained by reflection of the first propagation light from a reflected optical termination portion on a sample surface and a second reflected propagation light obtained by reflection of the second propagation light from a reflection plate of the optical termination portion is a target, although this will be described below in detail. In the phase shift interferometer using this reflection arrangement, since the propagation light reciprocates along an interference path, an amount of phase shift in only a forward path or a backward path is a half of the value of the phase described above. For example, when the phase shift is $\pi$ in reciprocation, the phase shift is $\pi/2$ in the forward path and the backward path, and when the phase shift is $\alpha$ in reciprocation, the phase shift is $\alpha/2$ in the forward path and the backward path.

Further, power $I_{int}(\lambda)\cos[\phi(\lambda)]$ of the cos interference component (phase shift 0) and power $I_{back}(\lambda)$ of the interference component that is the background component are given as Equation (2) below based on the interference spectrum, which the non-interference component overlaps, in the phase shifts of 0 and π in Equation (1).

$$\begin{pmatrix} I_{int}(v)\cos[\phi(v)] \\ I_{back}(v) \end{pmatrix} = \begin{pmatrix} \dfrac{I_0(v) - I_\pi(v)}{2} \\ \dfrac{I_0(v) + I_\pi(v)}{2} \end{pmatrix} \quad (2)$$

A process of obtaining the sin interference component (phase shift π/2) which is the other element of the two orthogonal components is performed according to the following procedure. First, using an addition theorem of a trigonometric function, the sin interference component is expressed as Equation (3) below.

$$I_{int}(\lambda)\sin[\phi(\lambda)] = \frac{1}{\sin\alpha}[I_{int}(\lambda)\cos[\phi(\lambda)]\cos\alpha - I_{int}(\lambda)\cos[\phi(\lambda) + \alpha]] \quad (3)$$

Equation (4) below is obtained by substituting the equation of the second row of Equation (2) into the equation of the third row of Equation (3) above.

$$I_{int}(\lambda)\cos[\phi(\lambda) + \alpha] = I_\alpha(\lambda) - I_{back}(\lambda) \quad (4)$$
$$= I_\alpha(\lambda) - \frac{I_0(\lambda) + I_\pi(\lambda)}{2}$$

Also, the cos component shown in the first row of Equation (2), and Equation (4) are substituted into Equation (3) to obtain Equation (5) below expressing the sin interference component.

$$I_{int}(\lambda)\sin[\phi(\lambda)] = \frac{1}{\sin\alpha}\left[\frac{I_0(\lambda) - I_\pi(\lambda)}{2}\cos\alpha - I_\alpha(\lambda) + \frac{I_0(\lambda) + I_\pi(\lambda)}{2}\right] \quad (5)$$

Next, using the equation of the first row of Equation (2), and Equation (5), the spectral phase φ(v) and the power spectrum $I_{int}(\lambda)$ are obtained as shown in Equations (6) and (7) below. Further, the power spectrum is equal to a square of the electric field intensity of the interference spectrum.

$$\phi(\lambda) = \tan^{-1}\left[\frac{\sin[\phi(\lambda)]}{\cos[\phi(\lambda)]}\right] \quad (6)$$
$$= \tan^{-1}\left[\frac{1}{\sin\alpha}\left\{\cos\alpha - \frac{2I_\alpha(\lambda) - I_0(\lambda) - I_\pi(\lambda)}{I_0(\lambda) - I_\pi(\lambda)}\right\}\right]$$

$$I_{int}(\lambda) = \quad (7)$$
$$\sqrt{\left\{\frac{I_0(\lambda) - I_\pi(\lambda)}{2}\right\}^2 + \frac{1}{\sin^2\alpha}\left\{\frac{I_0(\lambda) - I_\pi(\lambda)}{2}\cos\alpha - I_\alpha(\lambda) + \frac{I_0(\lambda) + I_\pi(\lambda)}{2}\right\}^2}$$

As described above, in the preferred embodiment, it is possible to obtain a change of the spectral phase from the two orthogonal components from which the non-interference component has been removed by measuring the interference spectrum that the non-interference component overlaps for the phase shifts of the three different values.

Configuration and Function of Chromatic Dispersion Measurement Apparatus

First Preferred Embodiment

Next, a configuration and a function of a phase shift interferometer in accordance with a first preferred embodiment will be described with reference to FIG. 1. FIG. 1 is a block diagram illustrating a configuration example of the phase shift interferometer in accordance with the first preferred embodiment.

In FIG. 1, the phase shift interferometer includes a light source 1, an incidence optical fiber 2 as an incidence path, an optical circulation unit 3, a connection optical fiber 4, a light branch and combination unit 5, a probe optical fiber 6 as a first light branch path, a sample measurement unit 7, a reference optical fiber 8 as a second light branch path, an optical phase shift unit 9 as an optical phase shifter, an optical delay unit 10, an optical termination portion 11, an emission optical fiber 12, an optical detection unit 13, a control unit 14, a data acquisition unit 15, wavelength sweep signal lines 16 and 17, a phase shift control line 18, a sampling clock signal line 19, and a detection signal line 20. Here, the length of a path through which light propagates in the phase shift interferometer is the length of an optical path of reciprocation from a fourth incidence and emission end 5c of the light branch and combination unit 5 to the optical termination portion 11 (or from a third incidence and emission end 5b of the light branch and combination unit 5 to the sample measurement unit 7) and from the optical termination portion 11 to the fourth incidence and emission end 5c of the light branch and combination unit 5 (or from the sample measurement unit 7 to the third incidence and emission end 5b of the light branch and combination unit 5).

The light source 1 is a wavelength variable laser which oscillates in a single longitudinal mode (oscillates at any wavelength to be given by a control value in a wavelength range in which oscillation can occur), and emits light to be used as propagation light from a first emission end 1a. In the first preferred embodiment, the laser oscillating in the single longitudinal mode is used because wavelength precision is degraded and noise due to mode interference (multimode light interference) or mode hop occurs when a laser oscillating in a multimode is used.

One end (a first end) of the incidence optical fiber 2 is connected to a first emission end 1a of the light source, and the other end (a second end) of the incidence optical fiber 2 is connected to a first incidence end 3a of the optical circulation unit 3. This incidence optical fiber 2 is an incidence optical path on which the propagation light emitted from the first emission end 1a of the light source 1 is incident from the first end, and which guides this incident propagation light from the second end to the first incidence end 3a of the optical circulation unit 3 (arrow S1).

Further, the propagation light reciprocatively propagates from a first incidence and emission end 3b of the optical circulation unit 3 to the first optical termination portion 11 of the reference optical fiber 8 or from the first incidence and emission end 3b of the optical circulation unit 3 to the sample measurement unit 7 of the probe optical fiber 7. Here, a description will be given on the assumption that the direction of a forward path through which propagation light propagates from the optical circulation unit 3 to the optical termination portion 11 or the sample measurement unit 7 via the light branch and combination unit 5 is a forward direction, and a backward path for return from the optical termination portion 11 or the sample measurement unit 7 to the optical circulation unit 3 via the light branch and combination unit 5 is a reflection direction (backward direction). Therefore, light reflected from the sample measurement unit 7 and then returned to the light branch and combination unit 5 relative to the first propagation light proceeding from the light branch and combination unit 5 to the sample measurement unit 7 is a first reflected propagation light, while light reflected from the optical termination portion 11 and returned to the light branch and combination unit 5 relative to the second propagation light proceeding from the light branch and combination unit 5 to the optical termination portion 11 is a second reflected propagation light. The polarization directions of the propagation light, the first propagation light, and the second propagation light propagating in the forward direction, the first reflected propagation light and the second reflected propagation light propagating in the reflection direction, and the combination light are all the same.

When the propagation light is incident from the first incidence end 3a connected to the second end of the incidence optical fiber 2 through the incidence optical fiber 2 in a forward direction, the optical circulation unit 3 emits this incident propagation light to the connection optical fiber 4 whose one end (a first end) is connected to a first incidence and emission end 3b (arrow S2), and emits combination light incident from a first end of the connection optical fiber 4 to the first incidence and emission end 3b in a reflection direction, to the emission optical fiber 12 whose one end (a first end) is connected to a second emission end 3c (arrow S12). An optical part used for this optical circulation unit 2 includes, for example, an optical fiber circulator including a polarization-maintaining optical fiber.

In the light branch and combination unit 5, a second incidence and emission end 5a is connected to the other end (a second end) of the connection optical fiber 4. The light branch and combination unit 5 branches the propagation light incident from the connection optical fiber 4 in two, in which one split light beam is a first propagation light and the other split light beam is a second propagation light. Further, the light branch and combination unit 5 emits the first propagation light from a third incidence and emission end 5b to the probe optical fiber 6 (arrow S3; propagation in the forward direction) and emits the second propagation light from the fourth incidence and emission end 5c to the reference optical fiber 8 (arrow S4; propagation in the forward direction).

In the light branch and combination unit 5, one end (a first end) of the probe optical fiber 6 is connected to the third incidence and emission end 5b, and one end (a first end) of the reference optical fiber 8 is connected to the fourth incidence and emission end 5c.

Therefore, the first propagation light and the first reflected propagation light propagate through the probe optical fiber 6, and the second propagation light and the second reflected propagation light propagate through the reference optical fiber 8.

In the sample measurement unit 7, the other end (a second end) of the probe optical fiber 6 is connected to a fifth incidence and emission end 7a. The first propagation light from the second end of the probe optical fiber 6 is incident on the fifth incidence and emission end 7a of the sample measurement unit 7 (arrow S3; propagation in a forward direction). Further, the first reflected propagation light that is reflected on a sample surface of the sample measurement unit 7 is emitted from the fifth incidence and emission end 7a of the sample measurement unit 7 to the second end of the probe optical fiber 6 (arrow S5; propagation in a reflection direction).

In the optical termination portion 11, the other end (termination) of the reference optical fiber 8 is connected to a sixth incidence and emission end 11a (a total reflection mirror). The second propagation light from the termination of the reference optical fiber 8 is incident on the sixth incidence and emission end 11a of the optical termination portion 11 (arrow S4; propagation in the forward direction). Further, second reflected propagation light obtained through total reflection of the first propagation light from the light reflection surface is emitted from the sixth incidence and emission end 11a of the optical termination portion 11 to the termination of the reference optical fiber 8 (arrow S7; propagation in a reflection direction).

Further, the light branch and combination unit 5 recombines the first reflected propagation light reflected by the sample surface inside the sample measurement unit 7 (arrow S5; propagation in the reflection direction) and then incident from the third incidence and emission end 5b with the second reflected propagation light reflected from the optical termination portion 11 and then incident from the fourth incidence and emission end 5c (arrow S7; propagation in the reflection direction). The light branch and combination unit 5 emits combination light obtained through combination, with polarization directions of the first propagation light and the second propagation light being the same, in order to acquire an interference component through recombination, from the second incidence and emission end 5a to the second end of the connection optical fiber 4 (arrow S11; propagation in the reflection direction).

In the reference optical fiber 8, an optical phase shift unit 9 and an optical delay unit 10 are interposed in series between the fourth incidence and emission end 5c of the light branch and combination unit 5 and the sixth incidence and emission end 11a of the optical termination portion 11. The arrangement order of the optical phase shift unit 9 and the optical delay unit 10 may be reversed.

This optical delay unit 10 is provided in the optical fiber having a shorter optical path length than the other optical fiber for the purpose of resolving an optical path length difference between the probe optical fiber 6 and the reference optical fiber 8 and gives a delay for adjustment to resolve the optical path length difference to the propagation light propagating through each optical fiber. In the first preferred embodiment, the optical delay unit 10 is provided, for example, in the reference optical fiber 8.

Thus, it is possible to reduce fluctuation of the optical path length occurring between the probe optical fiber 6 and the reference optical fiber 8 by providing the optical delay unit 10 and resolving the optical path length difference, and therefore it is possible to improve the measurement accuracy of the interference spectrum.

In the optical detection unit 13, the second end of the emission optical fiber 12 is connected to the second incidence end 13a. The optical detection unit 13 performs photoelectric conversion of combination light incident from the second end of the emission optical fiber 12 and outputs a result of the photoelectric conversion as an interference signal which is an electrical signal to the detection signal line 20.

Each of the incidence optical fiber 2, the connection optical fiber 4, the probe optical fiber 6 and the reference optical fiber 8 includes a polarization-maintaining single mode optical fiber having a propagation characteristic of a polarization-maintaining single mode in order to hold a polarization direction of input light and avoid measurement failure due to multimode interference. In the first preferred embodiment, the polarizations of the light propagating through the optical fibers constituting the phase shift interferometer are all the same.

The optical phase shift unit 9 is interposed on the path of the reference optical fiber 8, as described above. The optical phase shift unit 9 continuously changes the phase shift amount for phases of the second propagation light and the second reflected propagation light propagating through the reference optical fiber 8 from 0 to $3\pi/4$ in a first certain period. In other words, the optical phase shift unit 9 shifts the phase of the second propagation light between 0 and $3\pi/4$ in a forward path (the forward direction). Further, the optical phase shift unit 9 shifts the phase of the second reflected propagation light in a backward path (the reflection direction). Therefore, in the backward path in the reflection direction, a phase difference between the second reflected propagation light having passed the optical phase shift unit 9 and the first reflected propagation light is between 0 and $3\pi/2$.

Here, when the phase difference between the first reflected propagation light and the second reflected propagation light is 0, the optical detection unit 13 enters a 0 component detection mode. Further, when the phase difference between the first reflected propagation light and the second reflected propagation light is $\pi$, the optical detection unit 13 enters a $\pi$ component detection mode. Furthermore, when the phase difference between the first reflected propagation light and the second reflected propagation light is $\alpha$, the optical detection unit 13 enters an $\alpha$ component detection mode. Expressions of the respective first, second and third rows in the rows of the matrix of Equation (1) correspond to the interference spectra that the non-interference component overlaps, for interference components of the 0 component detection mode, the $\pi$ component detection mode, and the $\alpha$ component detection mode.

In the first preferred embodiment, when the second reflected propagation light has the phase shift (phase difference) of 0 relative to the first reflected propagation light, the interference of the 0 component occurs in the second reflected propagation light and the first reflected propagation light. Further, when the second reflected propagation light has the phase shift (phase difference) of $\pi$ relative to the first reflected propagation light, the interference of the $\pi$ component occurs in the second reflected propagation light and the first reflected propagation light. Similarly, when the second reflected propagation light has the phase shift (phase difference) of $\alpha$ relative to the first reflected propagation light, the interference of the $\alpha$ component is generated in the second reflected propagation light and the first reflected propagation light.

As a result, when the second reflected propagation light has the phase shift of 0 relative to the first reflected propagation light, the light branch and combination unit 5 emits the interference component in the 0 component of the first reflected propagation light and the second reflected propagation light as combination light from the second incidence and emission end 5a. Further, when the second reflected propagation light has a phase shift of $\pi$ relative to the first reflected propagation light, the light branch and combination unit 5 emits the interference component in the $\pi$ component of the first reflected propagation light and the second reflected propagation light as combination light from the second incidence and emission end 5a. Similarly, when the second reflected propagation light has the phase shift of $\alpha$ relative to the first reflected propagation light, the light branch and combination unit 5 emits the interference component in the $\alpha$ component of the first reflected propagation light and the second reflected propagation light as combination light from the second incidence and emission end 5a.

Further, a phase shifter using an electro-optical crystal (e.g., $LiNbO_3$) may be used for the optical phase shift unit 9. It is possible to continuously change the phase of the light passing through the optical phase shift unit 9 between 0 and $3\pi/2$ after reciprocation (after two passages) relative to the phase before the passage by continuously changing the phase shift voltage applied to the phase shifter in a first period. In the first preferred embodiment, the amount of the phase shift is continuously changed. However, the present invention is not limited thereto, and the phase shift unit 9 may be configured so that the amount of the phase shift is changed as a discrete value (e.g., by changing the phase into three values of $0 \to \alpha \to \pi$). Here, when the optical phase shift unit 9 shifts the phase of the second propagation light relative to the first propagation light or the phase of the second reflected propagation light relative to the first reflected propagation light, the optical phase shift unit 9 shifts the phase with the polarization direction being the same.

Further, it is unnecessary for the optical delay unit 10 to be separately provided if an optical path length difference between the probe optical fiber 6 and the reference optical fiber 8 does not affect measurement accuracy. Further, for convenience of decreasing the size of the entire interferometer, the optical phase shift unit 9 and the optical delay unit 10 may be provided on the probe optical fiber 6 rather than the reference optical fiber 8.

However, it is necessary for the light propagation time of the light propagation path with the interposed optical delay unit 10 to be shorter than that of the light propagation path on the other side. When it is necessary to install the delay unit 10 in one of the probe optical fiber 6 or the reference optical fiber 8 due to mechanic circumstances, the optical path length of the other optical fiber is set to be greater than that of the one optical fiber, and a delay time of the one optical fiber is delayed and adjusted by the delay unit 10 to correspond to the delay time of the other optical fiber.

Similarly, the optical phase shift unit 9 and the optical delay unit 10 may be provided in different propagation paths if the space for constituting the entire interferometer can be reduced by arranging the optical phase shift unit 9 and the optical delay unit 10 in spatially separated positions. In other words, the optical delay unit 10 is provided in the one having a shorter optical path length of light between the probe optical fiber 6 and the reference optical fiber 8, and the optical phase shift unit 9 is provided in the other optical fiber having a longer optical path length of light.

In this case, since the optical phase shift unit 9 or the optical delay unit 10 is placed in the propagation path to which the sample measurement unit 7 has been connected, it is necessary to pay attention to the design and assembly of the interference path so that increase in light loss or increase in reflection within the optical path does not occur.

Even when a connection order or an installation position of the optical phase shift unit 9 and the optical delay unit 10 is changed, there is no change in the measurement of the phase difference between the first reflected propagation light and the second reflected propagation light, as described above.

Further, for example, a reflecting mirror obtained by coating a silicon substrate or a glass substrate with a metal film such as Al (aluminum), Ag (silver) or Au (gold) or a dielectric film (a single-phase or a multi-layer) may be used as the optical termination portion 11. Further, a termination surface of the second end of the reference optical fiber 8 may be coated with a metal to form a reflection surface, and the reflection surface may be used as the optical termination portion 11.

Figure 2A:
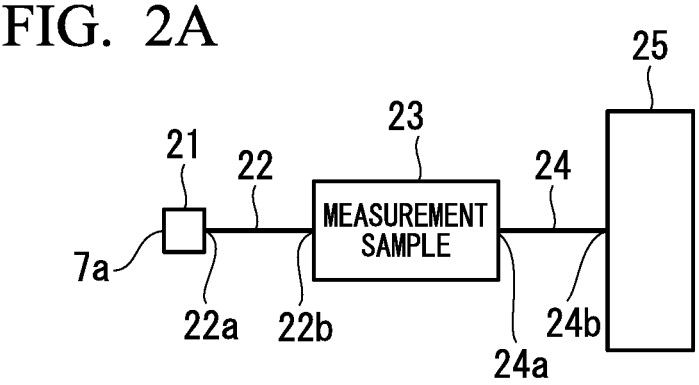
FIG. 2A is a diagram illustrating a configuration example of a sample measurement unit 7 in accordance with the first preferred embodiment of the present invention.
Figure 2B:
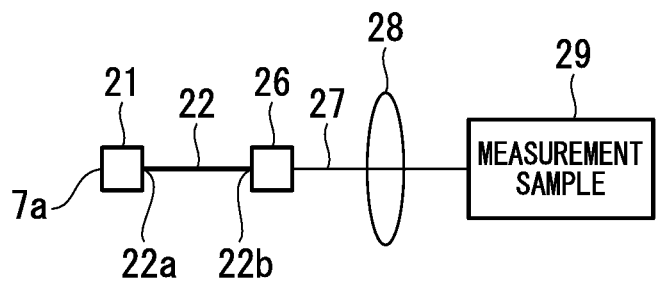
FIG. 2B is a diagram illustrating a configuration example of the sample measurement unit 7 in accordance with the first preferred embodiment of the present invention.

Then, FIGS. 2A and 2B are diagrams illustrating a configuration example of the sample measurement unit 7. A measurement sample is installed inside this sample measurement unit 7 as a measurement target.

FIG. 2A illustrates a configuration where a sample having a light transmission property is installed inside the sample measurement unit 7. A connector 21 to be connected with the second end of the probe optical fiber 6 is provided at the fifth incidence and emission end 7a of the sample measurement unit 7. Further, a first end 22a of an optical fiber 22 including a polarization-maintaining single mode optical fiber is connected to the connector 21 at a side opposite to the measurement sample (for transmission measurement) 23. A second end 22b of the optical fiber 22 and a side (incidence side) opposite to the connector 21 of the measurement sample (for transmission measurement) 23 are connected. A first end 24a of an optical fiber 24 including a polarization-maintaining single mode optical fiber is connected to a side (an emission side) of the measurement sample (for transmission measurement) 23 opposite to a reflection end 25. A second end 24b of the optical fiber 24 and the reflection end 25 are connected. For this reflection end 25, a total reflection mirror is used. The first propagation light is incident on the measurement sample (for transmission measurement) 23 through the optical fiber 22 and transmitted through this measurement sample (for transmission measurement) 23, and arrives at the reflection end 25 through the optical fiber 24. Also, the first propagation light reflected by the reflection surface of the reflection end 25 is returned as the first reflected propagation light in the reflection direction through the same path as the path along which the first propagation light has traveled, is incident on the measurement sample (for transmission measurement) 23 through the optical fiber 24, is transmitted through this measurement sample (for transmission measurement) 23, and arrives at the connector 21 through the optical fiber 22.

On the other hand, FIG. 2B illustrates a configuration when a sample having a light reflection property is placed inside the sample measurement unit 7. A connector 21 to be connected with the second end of the probe optical fiber 6 is provided in the fifth incidence and emission end 7a of the sample measurement unit 7. Further, a first end 22a of an optical fiber 22 including a polarization-maintaining single mode optical fiber is connected to the connector 21 on the side of a measurement sample 29 (for reflection measurement). A collimator 26 is connected to a second end 22b of the optical fiber 22. The collimator 26 emits the first propagation light incident from the optical fiber 22 as a space beam (the first propagation light) of a parallel light beam in a space. A lens 28 is arranged between the collimator 26 and the measurement sample (for reflection measurement) 29 and condenses the first propagation light to be incident vertically with respect to a surface of the measurement sample (for reflection measurement) 29. The first propagation light condensed by the lens 28 is radiated to the surface of the measurement sample (for reflection measurement) 29. Also, the first propagation light reflected by the surface of the measurement sample (for reflection measurement) 29 is returned as the first reflected propagation light in the reflection direction through the same path as the path along which the first propagation light has traveled, converted into a parallel light beam by the lens 28 again, and is incident on the optical fiber 22 through the collimator 22. Here, space propagation light 27 schematically indicates a path through which the propagation light is emitted from the collimator 26, reflected by the surface of the measurement sample (for reflection measurement) 29 and then returned to the collimator 26.

Figure 3:
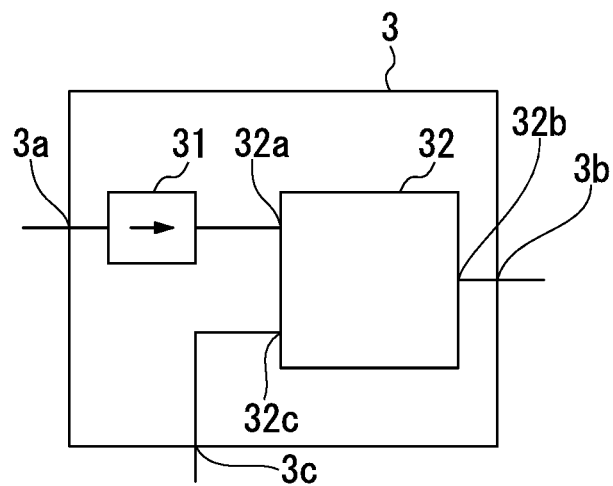
FIG. 3 is a diagram illustrating a configuration example of an optical circulation unit 3 in accordance with the first preferred embodiment of the present invention.

Further, FIG. 3 is a diagram illustrating a configuration example of the optical circulation unit 3. FIG. 3 illustrates a configuration example using optical parts other than an optical circulator. The optical circulation unit 3 of FIG. 3 includes an optical isolator 31 and a 2×1 optical coupler 32. This 2×1 optical coupler 32 emits a propagation light, which is incident from a terminal 32a corresponding to the first incidence end 3a, from a terminal 32b corresponding to the first incidence and emission end 3b. Further, the 2×1 optical coupler 32 emits combination light, which is incident from the terminal 32b corresponding to the first incidence and emission end 3b, from a terminal 32c corresponding to the second emission end to the emission optical fiber 12. Further, the optical isolator 31 is arranged in the terminal 32a corresponding to the first incidence end 3a so that the combination light is not returned as the reflected light to the light source 1 that emits the propagation light. Further, since the circulator has a narrow frequency band for propagation, the configuration of FIG. 3 enables a wide band to be covered for the optical circulator when a band to be measured is very wide.

The control unit 14 generates the phase shift voltage in synchronization with a wavelength sweep of the propagation light in the light source 1 and performs measurement of the interference spectrum. Therefore, the light source 1 and the control unit 14 are connected through the wavelength sweep signal line 17. Via the wavelength sweep signal line 17, the light source 1 transmits a trigger signal to the control unit 14 as an electrical signal for synchronization. Further, for the same purpose, the light source 1 is connected to the data acquisition unit 15 through the wavelength sweep signal line 16. Accordingly, the light source 1 transmits the trigger signal to the data acquisition unit 15 as an electrical signal for synchronization. This trigger signal is a signal indicating a start point of the wavelength sweep period in which the light source 1 performs the wavelength sweep.

The control unit 14 repeatedly outputs the phase shift voltage for causing the optical phase shift unit 9 to perform the phase shift as a control signal of a sinusoidal waveform to the optical phase shift unit 9 through the phase shift control line 18. In this case, the control unit 14 simultaneously outputs a sampling clock signal to the data acquisition unit 19 through the sampling clock signal line 19 in order to detect respective interference spectra having different phase components in synchronization with the phase shift voltage. As described above, the phase shift voltage is sent from the control unit 14 to the optical phase shift unit 9 through the phase shift control line connecting between the control unit 14 and the optical phase shift unit 9. The sampling clock signal is sent from the control unit 14 to the data acquisition unit 15 through the sampling clock signal line 19 connecting the control unit 14 with the data acquisition unit 15.

The optical detection unit 13 performs photoelectric conversion on the received incident combination light, and outputs a photoelectric conversion result as an interference signal to the data acquisition unit 15 through the detection signal line 20, which connects between the optical detection unit 13 and the data acquisition unit 15.

The electrical signal output from the optical detection unit 13 to the data acquisition unit 15 is an interference signal including a non-interference component (which the non-interference component overlaps), which is obtained by performing photoelectric conversion on the combination light incident from the emission optical fiber 12 into the electrical signal.

The control unit 14 continuously sequentially changes the phase shift voltage to be applied to the optical phase shift unit 9 in each first period, in synchronization with the trigger signal indicating a start point of the wavelength sweep period input through the wavelength sweep signal line 17. The control unit 14 supplies the phase shift voltage to the optical phase shift unit 9 through the phase shift control line 18 to cause the optical phase shift unit 9 to perform the shift phase.

In other words, when the measurement wavelength includes n points, the 0 component, the π component and the α component form one set for one wavelength, and therefore a process of sequentially changing the phase shift voltage within the first period Δt obtained by dividing the wavelength sweep period by the number of measurement sets n, in each first period Δt and switching the shift amount of the phase shift is performed in synchronization with the trigger signal.

Further, the data acquisition unit 15 continuously sequentially receives the interference signals of the 0 component, the π component and the α component from the optical detection unit 13 through the detection signal line 20 in synchronization with the first period Δt. For example, in the first preferred embodiment, it is assumed that the interference signals are periodically received in order of the 0 component→the α component→the π component in synchronization with the first period Δt. In the first period Δt, the phase shift voltage is continuously sequentially changed as the 0 component→the α component→the π component and this changing process is repeated in each first period within the wavelength sweep period of the light source 1.

Also, the data acquisition unit 15 obtains two orthogonal components in each wavelength, with interference elements of the 0 component, the π component and the α component acquired in time series forming one set, and uses the two orthogonal components as data for obtaining the spectral phase.

Figure 4:
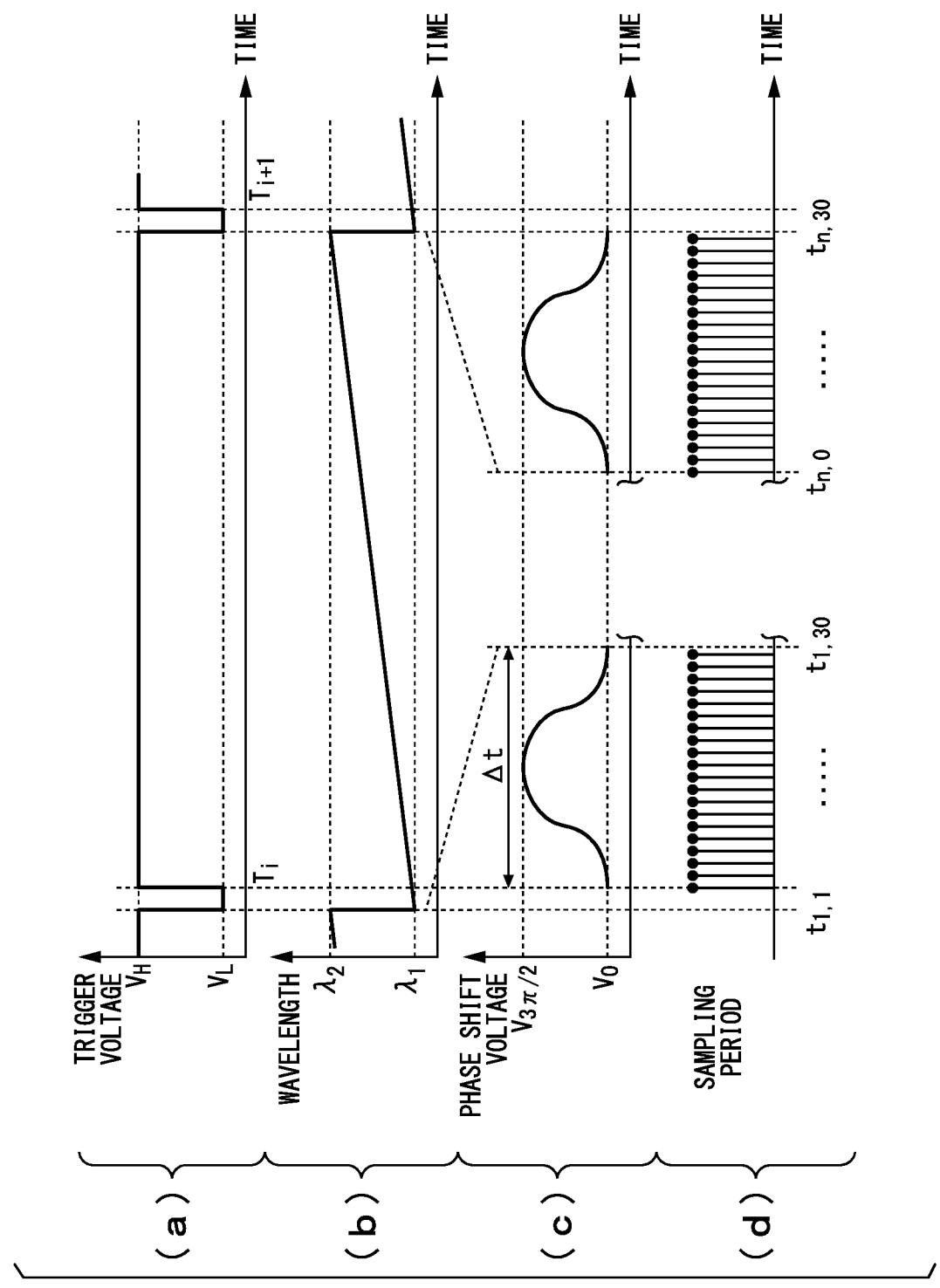
FIG. 4 is a waveform diagram illustrating a timing of a wavelength sweep operation of a light source 1, an operation of phase shift of an optical phase shift unit 9 corresponding to this wavelength sweep operation, and a phase shift voltage and a sampling clock signal generated by a control unit 14 in a phase shift interferometer in accordance with the first preferred embodiment of the present invention.

Next, FIG. 4 is a waveform diagram illustrating a timing of the wavelength sweep operation of the light source 1, an operation of the phase shift of the optical phase shift unit 9 corresponding to this wavelength sweep operation, and the phase shift voltage and the sampling clock signal generated by the control unit 14 in the phase shift interferometer in accordance with the first preferred embodiment.

An operation of measuring the spectral phase using the configuration of the phase shift interferometer illustrated in FIG. 1 in the first preferred embodiment will be described.

FIG. 4(*a*) is a diagram illustrating an output timing of the trigger signal output by the light source 1, in which a vertical axis indicates a voltage and a horizontal axis indicates time. In FIG. 4(*a*), each of an H level ($V_H$) and an L level ($V_L$) of the trigger signal output from the light source 1 is set to be suitable for TTL control (control using a TTL (Transistor Transistor Logic) interface).

FIG. 4(*b*) illustrates a temporal change in wavelength of light (propagation light) output in the wavelength sweep of the light source 1, in which a vertical axis indicates the wavelength and a horizontal axis indicates time. In FIG. 4(*b*), $\lambda_1$ is a wavelength of sweep start (a minimum wavelength in the range of measurement wavelength), and $\lambda_2$ is a wavelength of sweep stop (a maximum wavelength in the range of measurement wavelength). Therefore, a range between the wavelength $\lambda_1$ and the wavelength $\lambda_2$ is a range of the measurement wavelength, namely, a range in which the wavelength is swept.

FIG. 4(*c*) is a diagram illustrating a waveform of the phase shift voltage for changing a phase difference in the first period Δt, which is applied to the optical phase shift unit 9, in which a vertical axis indicates the voltage and a horizontal axis indicates time. A phase shift voltage $V_0$ is a voltage when the phase shift is 0 (a 0 component detection mode), and a phase shift voltage $V_{3\pi/2}$ is a voltage when the phase shift is 3π/2. The phase shift voltage consecutively and periodically changes in a range between $V_0$ and $V_{3\pi/2}$ as shown in FIG. 4(*c*) and is output from the control unit 14.

Since the phase shift interferometer in the first preferred embodiment is of a reflection type and the propagation light and the reflected propagation light propagate through the interference path twice in reciprocation, the phase shift occurs in each reciprocation and the phase shift voltage can be reduced to half of the phase shift voltage of a transmission-type interferometer. As the phase shift voltage is reduced to half of the phase shift voltage of the transmission-type interferometer, the voltage for controlling the phase shift output by the control unit 14 can be reduced and low power consumption can be achieved.

Further, the phase shift voltage $V_\pi$ is a voltage when the phase difference is π (a π component detection mode), and $V_\alpha$ is a voltage when the phase difference is α (an α component detection mode). In the first preferred embodiment, $V_\alpha$ is higher than $V_0$ and lower than $V_\pi$. In other words, $V_0 < V_\alpha < V_\pi$. The control unit 14 periodically changes the phase shift voltage in a sinusoidal shape in the first period Δt and applies the resultant phase shift voltage to the optical shift phase unit 9.

FIG. 4(*d*) is a diagram illustrating the sampling clock signal generated by the control unit 14, in which a vertical axis indicates the voltage and a horizontal axis denotes time. The sampling clock signal is a timing of the sampling period in which the data acquisition unit 15 receives the interference signal that the non-interference signal has overlapped, from the optical detection unit 13 as time-series data.

In FIGS. 4(*c*) and 4(*d*), time scales of the horizontal axes of FIGS. 4(*a*) and 4(*b*) are enlarged and only some time ranges are shown to clearly describe the first period Δt.

The light source 1 outputs the trigger signal to the control unit 14 and the data acquisition unit 15 in the wavelength sweep period of a trigger signal generation time "$T_{1+1} - T_1$" and also starts a sweeping process of linearly increasing the wavelengths from a wavelength λ1 to a wavelength λ2. Here, when a user measures a sweep change before actual measurement and detects that linearity of the swept wavelength over time is not achieved, calibration of the sweep wavelength is performed and nonlinearity of the wavelength sweep is corrected. Further, in the first preferred embodiment, while the wavelength is swept from a short wavelength side to a long wavelength side, the wavelength may be swept from the long wavelength to the short wavelength. Further, timing control is not limited to the TTL control and, for example, a CMOS (Metal Oxide Semiconductor) interface may be used.

Further, while the trigger voltage is set to transition from $V_L$ to $V_H$ when the wavelength sweep period starts and from $V_H$ to $V_L$ when the wavelength sweep period ends, as shown in FIG. 4(*a*), the trigger voltage may be set to transition in an opposite manner.

Further, the light source 1 may be configured to generate independence pulses having the same transition at the time of the start and the end of the wavelength sweep period.

Further, in the first preferred embodiment, the trigger signal is output to the data acquisition unit 15 through the wavelength sweep signal line 16 and to the control unit 14 through the wavelength sweep signal line 17. However, the trigger signal may be divided into a start trigger signal and an end trigger signal, two wavelength sweep signal lines may be provided for each of the data acquisition unit 15 and the control unit 14, and the start trigger signal and the end trigger signal may be output via different systems of wirings.

In the configuration described above, an optimal form may be selected according to a specification of the light source 1, the control unit 14 and the data acquisition unit 15.

When the trigger signal is supplied from the light source 1, the control unit 14 starts a process of continuously sequentially outputting the phase shift voltage from a voltage $V_0$ to a voltage $V_{3\pi/2}$ to the optical phase shift unit 9 in each first period Δt in synchronization with the trigger signal. In the first preferred embodiment, while the phase shift voltage from $V_0$ to $V_{3\pi/2}$ is supplied, the phase shift voltage may be supplied in reverse from $V_{V\pi/2}$ to $V_0$.

As a result, the optical phase shift unit 9 continuously sequentially changes the phase of the second propagation signal or the second reflection propagation signal propagating through the reference optical fiber 8 in the range from 0 to $3\pi/2$ after reciprocation based on the change from the supplied phase shift voltage $V_0$ to the phase shift voltage $V_{3\pi/2}$.

The optical detection unit 13 performs photoelectric conversion on the combination light having interference elements corresponding to each of the shift amounts 0, $\pi$ and $\alpha$ of the phase shift in each measurement wavelength according to the phase shift changing from 0 to $3\pi/2$ in each first period $\Delta t$, namely, in each measurement wavelength, and continuously supplies a resultant light to the data acquisition unit 15 as the interference signal.

Also, the data acquisition unit 15 samples the interference signal subjected to the photoelectric conversion according to a certain sampling timing transmitted in synchronization with the first period $\Delta t$, which is input from the control unit 14. By sampling the interference signal, each of an interference signal having an interference element of the 0 component, an interference signal having an interference element of the $\alpha$ component, and an interference signal having an interference element of the $\pi$ component in each wavelength can be obtained in this order. Here, the data acquisition unit 15 samples the interference signal in synchronization with a timing when the control unit 14 sequentially changes the phase shift voltage and outputs the respective phase shift voltages $V_0$, $V_\alpha$ and $V_\pi$, and obtains respective signals as the interference element of the 0 component, the interference element of the $\alpha$ component, and the interference element of the $\pi$ component.

In other words, as the control unit 14 continuously changes the phase amount of the phase shift of the second propagation light as $0 \to 3\pi/2 \to 0$ in the first period $\Delta t$, the data acquisition unit 15 can obtain interference elements of one set of 0 component, $\alpha$ component and $\pi$ component corresponding to one measurement period in this order. From the obtained interference elements, n sets of interference elements of the 0, $\alpha$ and $\pi$ components are obtained from n first periods $\Delta t$ in the range of the measurement wavelength.

Thus, as the phase amount of the phase shift of the second propagation light continuously changes as $0 \to 3\pi/2 \to 0$, the data acquisition unit 15 acquires, in each sampling clock signal, an interference signal of one point corresponding to the phase amount at that time point. Therefore, the data acquisition unit 15 acquires the interference signals of one set of phase components of 0, $\alpha$ and $\pi$ based on three sampling clock signals.

As a result, the n sets of interference elements (interference signals) of the 0, $\alpha$ and $\pi$ components can be obtained from the n first periods $\Delta t$ within the range of the measurement wavelength.

Further, the data acquisition unit 15, for example, performs sampling of 30 points while the phase shift voltage changes as $0 \to 3\pi/2 \to 0$ in the first period in order to improve determination precision of each of the phase shift amounts 0, $\alpha$ and $\pi$. In other words, in the first preferred embodiment, the data acquisition unit 15 acquires the interference fringe data of thirty components having different shift amounts corresponding to thirty types of interference signals in one first period $\Delta t$.

Also, when obtaining the spectral phase $\phi(\lambda)$ and the power spectrum $I_{int}(\lambda)$, the data acquisition unit 15 extracts, from the plurality of sampled interference fringe data, three types corresponding to the 0 component, the $\pi$ component and the $\alpha$ component from the interference fringe data of thirty components based on a timing at which each of the phase shift voltages $V_0$, $V_\alpha$ and $V_\pi$ has been output, and substitutes the three types into Equations (6) and (7). Here, when the measurement wavelength includes n points, a total sampling number is 30×n (light components) by sweeping the wavelength once in the wavelength sweep period.

As described above, the data acquisition unit 15 samples and measures the interference elements of the 0 component, the $\alpha$ component and the $\pi$ component based on a sampling period of a regular interval, as described above. Therefore, one system of a reception port which receives the sampling clock signal (electrical signal) to be used for sampling and the combination light may be provided in the data acquisition unit 15, and the phase shift interferometer can be configured simply.

In FIG. 4(d), measurement points of the first measurement wavelength when sampling is performed twenty times in each first period of the n measurement wavelengths, namely, sampling timings $t_{n,1}$ to $t_{1,20}$ and the measurement points of the $n^{th}$ measurement wavelength, namely, sampling timings $t_{n,1}$ to $t_{n,20}$, are illustrated.

Here, when there are 30 measurement points at which the sampling is performed within each of the first periods $\Delta t$, a change in the sweep wavelength at each measurement point cannot be neglected. Therefore, it is necessary to correct the change in the sweep wavelength at each measurement point within each of the first periods $\Delta t$, and maintain the wavelength precision of each of the obtained interference fringe data. In the first preferred embodiment, a configuration in which the linear interpolation based on n measurement values of the sampling timing which is the measurement wavelength having the same order in each of the first periods $\Delta t$ in the 30×n measurement values within the wavelength sweep period is performed in each same order to calculate the interference fringe data of thirty components in each sampling timing is provided in the data acquisition unit 15. Therefore, the data acquisition unit 15 includes a memory which stores a program for performing the above-described linear interpolation or a circuit for executing the linear interpolation.

Accordingly, the interpolation process in which the measurement interval of each wavelength component is $\frac{1}{30}$ is performed on each of phase components, and the number of data points of the interference signal for each phase component increases by a factor of 30, thereby improving the measurement accuracy of the spectral phase. Since the sweep of the wavelength is performed linearly, it is possible to determine the phase amount corresponding to the measurement wavelength over time based on a linear relationship. As a result, it is possible to easily interpolate the interference fringe data corresponding to each phase component.

Further, although not described in FIG. 1, the phase shift interferometer of the first preferred embodiment includes a storage unit which stores 30×n measured interference fringe data, which is used to perform the linear interpolation. The data acquisition unit 15 sequentially writes and stores the 30×n measured interference fringe data together with identification information (e.g., sampling timing $t_{i,j}$ indicating an $j^{th}$ measurement point in the $i^{th}$ first wavelength described above) to and in the storage unit, and reads each interference fringe data to perform linear interpolation at a time point at which the wavelength sweep period ends. Here, i is an integer equal to or more than 1 and equal to and less than n ($1 \le i \le n$), and j is an integer equal to or more than 1 and equal to or less than 30 ($1 \le j \le 30$).

In FIG. 4(d), interference fringe data measured in each of sampling timings $t_{i,1}$, $t_{i,6}$, and $t_{i,11}$ corresponds to each of the 0 component when the shift amount of the phase shift is 0, the α component when the shift amount of the phase shift is α, and the π component when the shift amount of the phase shift is π. Here, the data acquisition unit 15 performs phase calibration of the phase amount of the α component used for calculation of the spectral phase $\phi(\lambda)$.

For example, in the first preferred embodiment, the phase calibration of the phase amount corresponding to the sampling time $t_{i,6}$ is performed, and the phase amount in the sampling time $t_{i,6}$ is 0.4184367π in radians.

Phase calibration for the α component in each measurement wavelength is performed through curve fitting. In other words, the phase amount of each phase component can be obtained by executing curve fitting for thirty interference data in each wavelength using a trigonometric function as a fitting function. In this case, if the generated phase shift ranges from 0 to 3π/2, thirty interference components in each measurement wavelength include (cover) all amplitudes from a maximum interference value to a minimum interference value in the measurement range. This can enable the phase calibration for the α component in all measurement wavelengths.

For a phase calibration method, a plurality of algorithms for phase calibration are described in Non-Patent Document 1, but the algorithm for phase calibration based on the curve fitting using the trigonometric function as the fitting function as in the first preferred embodiment is not described. Therefore, in the first preferred embodiment, since the phase shift of the sine wave illustrated in FIG. 4(c) is performed by the curve fitting using the trigonometric function as the fitting function, the phase calibration can be performed with high precision in a short time.

Further, when the number of sampling points is small (when the number is smaller than 30 in the first preferred embodiment), precision of the interpolation of the interference fringe data described above is degraded and determination precision of 0, α and π which are the shift amount of the phase shift deteriorates. Therefore, a ripple is generated in a result of calculating the spectral phase $\phi(\lambda)$ or the power spectrum $I_{int}(\lambda)$ (a graph in which each of the spectral phase $\phi(\lambda)$ or power spectrum $I_{int}(\lambda)$ is plotted on a vertical axis, in which a horizontal axis indicates a wavelength).

Further, even when the number of decimal places is small when the phase amount obtained through the phase calibration is a (when precision of the phase calibration is low), a ripple is generated in the result of calculating the spectral phase $\phi(\lambda)$ or the power spectrum $I_{int}(\lambda)$.

In the first preferred embodiment, relative intensity of the ripple is calculated as the number of the sampling points (30 points in the first period) and a number (six) of decimal places of the phase amount of a calibrated sampling time $t_{i,6}$ to be less than 1 ppm of an actual measurement value of each of the spectral phase $\phi(\lambda)$ and the power spectrum $I_{int}(\lambda)$.

Further, in the first preferred embodiment, the number of interference components within the first period Δt, namely, the sampling points, is 30, and the number of calculation digits of the phase amount α is 6 decimal places. However, the present invention is not limited to these numbers of sampling points and decimal places, and a degree of reduction of the relative intensity of the ripple may be determined and set according to an allowed degree of the necessary relative intensity of the ripple, and the numbers of sampling points and decimal places may be set. Further, it is understood that the number of decimal places of the number of the calculation digits of the phase amount π should also be determined and set according to reduction of the relative intensity of the ripple, similar to the phase amount α.

Further, in the first preferred embodiment, the interference signal measured in the sampling time $t_{i,6}$ was used as interference fringe data of the phase amount a described above. However, the present invention is not limited to this sampling time, and any of 30 measurements may be used if the phase shift is the phase shift other than the phase amounts 0 and π. Here, if the phase amounts of the phase shift are not adjacent values, an error of the phase amount is reduced and therefore influence on the relative intensity of the ripple is less.

Therefore, the relative intensity of the ripple may be observed in each sampling time $t_{i,j}$ and it may be determined whether a sampling time in which the relative intensity of the ripple is in a necessary allowable range is to be used for sampling of the phase amount α.

For example, when the number n of first periods is 1000 and the wavelength sweep period $T_{1+1}-T_1$ is 1 s (second), the first period $\Delta_t$ which is a switching period for the phase shift voltage is 1 ms if one second is divided by n, i.e., 1000. Further, if the time 1 ms of the first period is divided by the number 30 of measurement points (sampling points) in the first period Δt, an interval of the sampling timing is about 33 μs. As described above, through the linear interpolation, a total number of interference fringe data of the component of each phase amount of the phase shift is 30000 by multiplying n by 30.

As described above, based on the first preferred embodiment, the phase shift interferometer for performing high-precision spectral phase measurement which can be applied to chromatic dispersion measurement and tomographic image measurement in optical coherence tomography can be realized by a configuration which is easily reduced in size, configured simply, and manufactured at lower cost as compared to a conventional one.

Further, in the first preferred embodiment, the data acquisition unit 15 samples interference elements of the 0, α and π components in the sampling period of a regular time interval to perform measurement.

Therefore, according to the first preferred embodiment, one system of reception port for receiving the sampling clock signal (electrical signal) used for sampling and the combination light may be provided in the data acquisition unit 15. A meter can be simply configured.

Second Preferred Embodiment

Next, a phase shift interferometer in accordance with a second preferred embodiment of the present invention will be described. The second preferred embodiment has a configuration similar to the first preferred embodiment, but a set of 0 component, α component and π component are received in parallel via three reception ports (reception ports P1, P2 and P3 which will be described below) provided in parallel in the data acquisition unit 15 in the configuration of FIG. 1.

Figure 5:
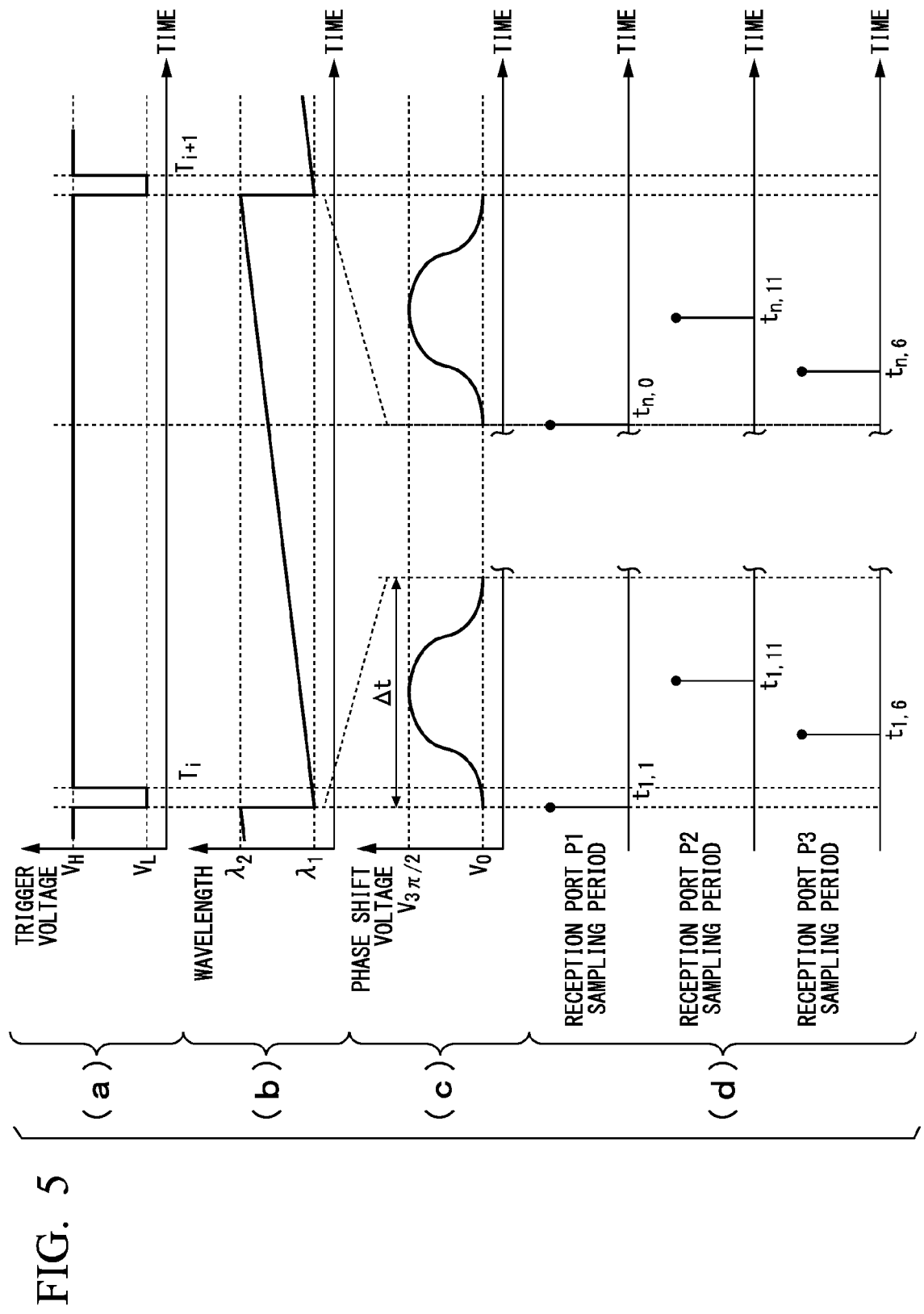
FIG. 5 is a waveform diagram illustrating a timing of a wavelength sweep operation of the light source 1, a phase shift operation of the optical phase shift unit 9 corresponding thereto, and a sampling operation for an interference signal from an optical detection unit 13 in a data acquisition unit 15 in a phase shift interferometer in accordance with a second preferred embodiment of the present invention.

FIG. 5 is a waveform diagram illustrating a timing of a wavelength sweep operation of the control unit 14, a phase shift operation of the optical phase shift unit 9 corresponding thereto, and a sampling operation for the interference signal from the optical detection unit 13 in the data acquisition unit 15.

FIG. 5(a) is a diagram illustrating an output timing of the trigger signal output by the light source 1, in which a vertical axis indicates a voltage and a horizontal axis indicates time. In FIG. 5(a), each of an H level and an L level of the trigger signal output from the light source 1 are set to be suitable for TTL control.

FIG. 5(b) illustrates a temporal change of the wavelength of the light output in the wavelength sweep of the light source 1, in which a vertical axis indicates the wavelength and a horizontal axis indicates time. In FIG. 5(b), $\pi_1$ is a wavelength of sweep start (a minimum wavelength in the range of measurement wavelength), and $\lambda_2$ is a wavelength of sweep stop (a maximum wavelength in the range of measurement wavelength).

FIG. 5(c) is a diagram illustrating a waveform of the phase shift voltage, which changes, in the first period $\Delta t$, a phase difference to be applied to the optical phase shift unit 9, in which a vertical axis indicates the voltage and a horizontal axis indicates time. A phase shift voltage $V_0$ is a voltage when the phase difference is made to be 0 (a 0 component detection mode), and a phase shift voltage $V_{3\pi/2}$ is a voltage when the phase difference is made to be $3\pi/2$. Further, a phase shift voltage $V_\pi$ is a voltage when the phase difference is made to be $\pi$ (a $\pi$ component detection mode), and a phase shift voltage $V_\alpha$ is a voltage when the phase difference is made to be $\alpha$ (an $\alpha$ component detection mode). Further, the phase shift voltage for performing detection of the 0 component, the $\alpha$ component and the $\pi$ component is sinusoidally changed within the first period. In the second preferred embodiment, $\alpha$ is a phase amount shown in radians and is a real number for which $0<\alpha<\pi$. Therefore, $\alpha$ changes in the range of $0<\alpha<\pi$. Therefore, the control unit 14 changes the phase shift voltage in a periodically sinusoidal shape in response to in the first period $\Delta t$ and supplies the phase shift voltage to the optical shift phase unit 9.

FIG. 5(d) is a diagram illustrating a timing of the sampling period in which the control unit 14 receives the interference signal from the optical detection unit 13 as time-series data in parallel from the reception port P1, the reception port P2, and the reception port P3, in which a vertical axis indicates the voltage and a horizontal axis indicates time. In the second preferred embodiment, the reception port P1 receives the interference signal of the 0 component, the reception port P2 receives the interference signal of the $\pi$ component, and the reception port P3 receives the interference signal of the $\alpha$ component.

In FIGS. 5(c) and 5(d), time scales of the horizontal axes of FIGS. 5(a) and 5(b) are enlarged and only some time ranges are illustrated in order to clearly describe the first period $\Delta t$.

When the control unit 14 is outputting the phase shift voltage $V_0$, the data acquisition unit 15 receives the interference signal of the 0 component subjected to the photoelectric conversion from the optical detection unit 13 via the reception port P1. Further, when the control unit 14 is outputting the phase shift voltage $V_\pi$, the data acquisition unit 15 receives the interference signal of the $\pi$ component subjected to the photoelectric conversion from the optical detection unit 13 via the reception port P2. Further, when the control unit 14 is outputting the phase shift voltage $V\alpha$, the data acquisition unit 15 receives the interference signal of the $\alpha$ component subjected to the photoelectric conversion from the optical detection unit 13 via the reception port P3.

In the second preferred embodiment, the number n of the first periods $\Delta t$ in the wavelength sweep period is 1000 and the wavelength sweep period is 1 s, similar to the first preferred embodiment. A sampling period of each of the reception port P1, the reception port P2 and the reception port P3 is 1 ms.

The data acquisition unit 15 performs A/D (analog/digital) conversion to acquire a voltage level of the interference signal from the optical detection unit 13 as digital data (interference fringe data).

Therefore, an operation speed of an A/D conversion circuit in the data acquisition unit 15 is likely to be a limiting factor when the sampling period is desired to be shortened.

However, in the second preferred embodiment, as the parallel reception of three systems of reception port P1, reception port P2 and reception port P3 is adopted, the sampling speed of each reception port is one third of the sampling speed when the reception is performed using only one port, and therefore, a limit of the operation speed of the A/D conversion circuit increases threefold, thereby shortening the measurement time.

Further, since it is unnecessary to sequentially divide measurement timing of the 0 component, the $\alpha$ component and the $\pi$ component in one reception port, a data processing program can be simplified and the data processing speed can be improved.

Third Preferred Embodiment

Figure 6:
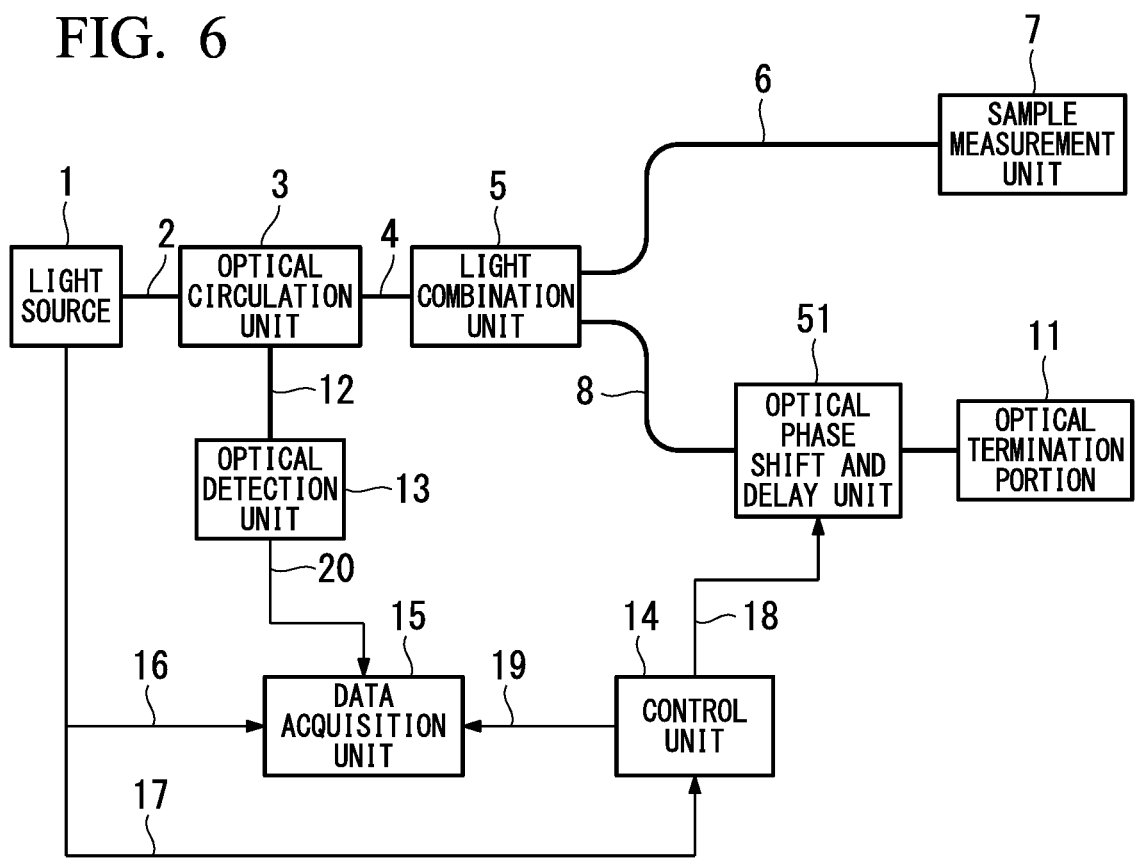
FIG. 6 is a block diagram illustrating a configuration example of a phase shift interferometer in accordance with a third preferred embodiment of the present invention.

Next, a chromatic dispersion measurement apparatus in accordance with a third preferred embodiment of the present invention will be described. FIG. 6 is a block diagram illustrating a configuration example of a phase shift interferometer in accordance with the third preferred embodiment. The same components as those of the first preferred embodiment are denoted by the same reference signs and a configuration different from the first preferred embodiment will be described.

When the optical delay unit 7 which resolves an optical path length difference between the first optical fiber 5 and the second optical fiber 6, and the optical phase shift unit 8 which shifts the phase of the propagation light are used, the optical delay unit 7 and the optical phase shift unit 8 are connected to different optical fibers in the case of the first preferred embodiment.

As can be seen from a comparison with the configuration of the first preferred embodiment illustrated in FIG. 1, it is unnecessary to provide each of the optical phase shift unit 9 and the optical delay unit 10 in the different optical fibers. Therefore, in the third preferred embodiment, an optical phase shift and delay unit 51 having a function of shifting the phase difference of the light of the optical phase shift unit 9 and a function of delaying the propagation of the light of the optical delay unit 10 by integrally unifying the optical phase shift unit 9 and the optical delay unit 10 in the first preferred embodiment is provided in any one of the probe optical fiber 6 and the reference optical fiber 8. When any one of the probe optical fiber 6 and the reference optical fiber 8 has a shorter optical path length than the other optical fiber, the optical phase shift and delay unit 51 is provided in the one optical fiber to correct the optical path length difference with the other optical fiber. Thus, using the optical phase shift and delay unit 51 obtained by unifying the optical phase shift unit 9 and the optical delay unit 10, it is possible to reduce the size of the apparatus in comparison with the apparatus in the first preferred embodiment.

Further, it is possible to reduce light loss due to connector coupling by integrally unifying the optical phase shift unit 9 and the optical delay unit 10. As a result, it is possible to cause the power of the light source 1 to have a lower level than that in the first preferred embodiment and to reduce consumption of energy in the light source 1.

Further, when the power of the light source 1 is the same as that in the first preferred embodiment, it is possible to evaluate a phase shift spectrum of a measurement sample in which the light loss is higher than that in the first preferred embodiment.

Furthermore, when a direct current voltage component is added to the phase shift voltage to be applied from the control unit 14 to the optical phase shift unit 9, it is possible to control delay time of the propagation light of the optical fiber through direct current phase shift. Therefore, it is possible to resolve the optical path difference between the probe optical fiber 6 and the reference optical fiber 8 with high precision through control of the delay time based on the voltage and to precisely control phase stability in comparison with the first preferred embodiment.

Fourth Preferred Embodiment

A procedure of using the phase shift interferometers shown in the first to third preferred embodiments to evaluate chromatic dispersion of an optical part will be described. In this evaluation of the chromatic dispersion, when the evaluation of chromatic dispersion in transmission is performed, the configuration illustrated in FIG. 2A is used as a configuration of the sample measurement unit 7. On the other hand, when the evaluation of chromatic dispersion in reflection is performed, the configuration illustrated in FIG. 2B is used as configuration of the sample measurement unit 7.

In order to evaluate the chromatic dispersion, it is necessary to obtain a dispersion parameter as follows.

When the dispersion parameter is obtained, the spectral phase $\phi(\lambda)$ obtained as a function of a wavelength $\lambda$ is converted to a spectral phase $\phi(\nu)$ which is a function of a frequency $\nu$.

Also, a change $\Delta\phi(\nu)$ of the spectral phase is calculated as a difference in spectral phase between adjacent frequencies from the spectral phase $\phi(\nu)$ obtained as a function of frequency. Here, when a distance between the adjacent frequencies is $\Delta\nu$, a dispersion parameter D is obtained by Equation (8) below. In Equation (8), $\nu$ denotes frequency, c denotes speed of the light, and L denotes light propagation distance (path length of the interference path).

$$D \simeq -\frac{1}{2\pi c} \frac{\Delta\phi(\nu)}{L} \left(\frac{\nu}{\Delta\nu}\right)^2 \qquad (8)$$

The data acquisition unit 15 in FIG. 1 or 6 includes a conversion unit which converts a spectral phase $\phi(\lambda)$ which is a function of a wavelength into a spectral phase $\phi(\nu)$ which is a function of a frequency, a data storage unit which stores the converted spectral phase $\phi(\nu)$, a difference calculation unit which sequentially reads the spectral phase of an adjacent frequency from the data storage unit and calculates a change $\Delta\phi(\nu)$ in the spectral phase for each $\Delta\nu$, and a dispersion parameter calculation unit which calculates a dispersion parameter from the change $\Delta\phi(\nu)$ of this spectral phase using Equation (8).

Further, a configuration in which a program which instructs the data acquisition unit 15 to perform calculation of the change $\Delta\phi(\nu)$ in the spectral phase and calculation of the dispersion parameter is stored in a program storage unit, and an operation processor including an MPU (Micro Processing Unit) executes this program may be used instead of providing the difference calculation unit and the dispersion parameter calculation unit in the data acquisition unit 15. In this case, the operation processor performs the calculation of the change $\Delta\phi(\nu)$ in the spectral phase and the calculation of the dispersion parameter according to the program stored in the program storage unit.

Fifth Preferred Embodiment

A procedure for obtaining the tomographic image of the optical coherence tomography using the phase shift interferometer shown in the first and third preferred embodiments will be described. When this tomographic image of the optical coherence tomography is obtained, the configuration illustrated in FIG. 2B is used as a configuration of the sample measurement unit 7 in order to obtain a reflection from a surface (a sample surface) of a sample which is a measurement target. In this configuration, only the tomographic image in the depth direction at a certain point of the sample surface is obtained. Therefore, the lens 28 is moved two-dimensionally in parallel to the sample surface. In other words, a driving mechanism which moves the lens 28 in parallel along a line on a two-dimensional plane which is in parallel to a surface of a stage having a sample placed thereon is provided in the sample measurement unit 7 to drive the lens 28 in parallel along the line on the two-dimensional plane, such that a spectral phase at each measurement point on the line, namely, at each coordinate point coordinate point, can be detected.

Further, the driving mechanism may be configured to move the stage having the sample placed thereon in parallel instead of moving the lens 28 in parallel.

Also, in order to obtain the tomographic image of the sample from the spectral phase, the spectral phase $\phi(\lambda)$ which is a function of a wavelength is converted into a spectral phase $\phi(\nu)$ which is a function of a frequency, similar to the case of the fourth preferred embodiment.

Next, a spectral phase $\phi(\nu)$ inverse Fourier transform at each measurement point of the line moved in parallel on the two-dimensional plane is performed on the obtained spectral phase $\phi(\nu)$ in a frequency notation to convert the spectral phase from a frequency domain to an image space domain and generate image data that is a tomographic image in a depth direction at each measurement point. Here, when the inverse Fourier transform of the spectral phase $\phi(\nu)$ is performed, in inverse Fourier transform data obtained through the inverse Fourier transform of the spectral phase $\phi(\nu)$, a horizontal axis indicates time and a vertical axis indicates intensity of reflected reflection light. The propagation distance in a reciprocation path for the light (the first propagation light) in the reflection of the sample surface is obtained by multiplying this time by the speed of the light.

In other words, half of this propagation distance becomes a detection value corresponding to each position in the depth direction in the sample. Therefore, the tomographic image of the sample is obtained by plotting the intensity in each inverse Fourier transform data with respect to the position which is half of the propagation distance at each measurement point on the line moved in parallel on the two-dimensional plane.

Further, a three-dimensional tomographic image of the sample can be obtained by performing a process of moving the lens 28 in parallel along the two-dimensional plane which is in parallel to the surface of the stage having the sample placed thereon, detecting the spectral phase $\phi(\nu)$ at each measurement point and obtaining the tomographic image described above, at each measurement point on the two-dimensional plane.

In order to obtain the tomographic image described above, in the fifth preferred embodiment, the data acquisition unit 15 includes a control unit which controls the driving mechanism which moves the lens 28 in parallel along the two-dimensional plane, which is parallel to the surface of the stage having the sample placed thereon for acquisition of the tomographic image, the calculation unit which calculates the phase spectral phase $\phi(\nu)$ obtained at each measurement point on the two-dimensional plane and stores the phase spectral phase at each measurement point in the storage unit, a conversion unit which reads the spectral phase $\phi(\nu)$ at each measurement point from the storage unit and performs an inverse Fourier transform, and a tomographic image generation unit which obtains the propagation distance of the light and plots the intensity in the inverse Fourier transform data with respect to positions which are half of the obtained propagation distance.

Further, a program storage unit having a program stored therein for causing an MPU to execute the functions of the control unit, the calculation unit, the conversion unit, and the tomographic image generation unit described above may be provided, and a CPU may sequentially read and execute the program from the program storage unit to perform the processes of the control unit, the calculation unit, the conversion unit and the tomographic image generation unit.

According to the preferred embodiment, it is possible to easily apply the phase shift interferometer to the optical coherence tomography and to detect the spectral phase $\phi(\lambda)$ with high precision. Thus, it is possible to obtain a high-resolution, three-dimensional tomographic image.

While preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

The present invention can be widely applied to a phase shift interferometer (a phase shift fiber spectrum interferometer) for performing measurement of chromatic dispersion and tomographic photography in optical coherence tomography.

What is claimed is:

1. A phase shift interferometer, comprising:
a light source that includes a first emission end, is configured to generate propagation light by performing wavelength sweep of light in a single longitudinal mode, and emits the propagation light from the first emission end;
an incidence optical path that includes one end connected to the first emission end, the incidence optical path including a single mode optical fiber having a polarization-maintaining characteristic, which propagates the propagation light;
an optical circulation unit that includes a first incidence end, a first incidence and emission end, and a second emission end, the first incidence end being connected to the other end of the incidence optical path, and the propagation light incident from the first incidence end being emitted from the first incidence and emission end or combination light incident from the first incidence and emission end being emitted from the second emission end;
a connection path that includes one end connected to the first incidence and emission end, the connection path including a single mode optical fiber having a polarization-maintaining property;
an optical beam splitting and combining unit having a second incidence and emission end, a third incidence and emission end, and a fourth incidence and emission end, the second incidence and emission end being connected to the other end of the connection path, and the optical beam splitting and combining unit splitting the propagation light incident from the second incidence and emission end into first propagation light and second propagation light having the same polarization as the first propagation light, emitting the first propagation light from the third incidence and emission end, emitting the second propagation light from the fourth incidence and emission end, combining first reflected propagation light incident from the third incidence and emission end with a second reflected propagation light incident from the fourth incidence and emission end to generate the combination light that is an interference result, and emitting the combination light from the second incidence and emission end;
a probe optical path having one end connected to the third incidence and emission end, the probe optical path including a single mode optical fiber having a polarization-maintaining property;
a reference optical path having one end connected to the fourth incidence and emission end, the reference optical path including a single mode optical fiber having a polarization-maintaining property;
a sample measurement unit that includes a fifth incidence and emission end, the fifth incidence and emission end being connected to the other end of the probe optical path, and the sample measurement unit reflecting the first propagation light incident from the fifth incidence and emission end, from a sample surface of a measurement target arranged therein to generate the first reflected propagation light, and emitting the first reflected propagation light from the fifth incidence and emission end;
an optical termination portion that includes a sixth incidence and emission end and a reflection surface, the sixth incidence and emission end being connected to the other end of the reference optical path, and the optical termination portion totally reflecting the second propagation light incident from the sixth incidence and emission end in the reflection surface to generate the second reflected propagation light, and emitting the second reflected propagation light from the sixth incidence and emission end;
an optical phase shift unit that is provided in one of the probe optical path and the reference optical path and performs phase shift of the light propagating through the one optical path by a phase shift amount $\alpha_i/2$ (in radians; $\alpha_i$ is a real number, $0 \leq \alpha_i \leq 3\pi/2$, i is an integer, and $3 \leq i$), and periodically changes the phase shift amount $\alpha_i/2$;
an emission optical path that includes one end connected to the second emission end, the emission optical path including a single mode optical fiber to propagate the combination light;
an optical detection unit that includes a second incidence end, the other end of the emission optical path being connected to the second incidence end, and an optical detection unit converting the combination light incident from the second incidence end into an electrical signal to generate an interference signal and outputting the interference signal;
a control unit that controls a period for controlling the phase shift amount and the phase shift in the optical phase shift unit whenever the wavelength sweep is performed, in synchronization with the wavelength sweep, and generates a sampling signal for acquiring in time series order the interference signal corresponding to an $i^{th}$ light component in order in which i is incremented within one period of the phase shift; and
a data acquisition unit that acquires in time series order the interference signal corresponding to the $i^{th}$ light component whenever the sampling signal is supplied.

2. The phase shift interferometer according to claim 1, wherein
a range of values that i can have is m, and
the control unit performs an interpolation process in which a measurement interval of each wavelength component is 1/m, on each of the $i^{th}$ light components, such that the number of data points of all interference signals increases by a factor of m.

3. The phase shift interferometer according to claim 1, wherein
a total number of $\alpha_i$ elements is equal to or more than 3 (i≥3), and
the control unit extracts, from the elements, a first light component of a phase $\alpha_1$, a second light component of a phase $\alpha_2$ and a third light component of a phase $\alpha_3$ as three elements, and acquires the interference signal from each of the first light component, the second light component and the third light component.

4. The phase shift interferometer according to claim 3, wherein the total number of $\alpha_i$ elements is equal to or more than 30 (i≥30).

5. The phase shift interferometer according to claim 1, further comprising:
an optical delay unit provided in one of the probe optical path and the reference optical path to adjust an optical path length difference between the probe optical path and the reference optical path.

6. The phase shift interferometer according to claim 5, wherein the optical delay unit is provided in the one of the probe optical path and the reference optical path, and the optical phase shifter is provided in the other of the probe optical path and the reference optical path.

7. The phase shift interferometer according to claim 5, wherein the optical delay unit and the optical phase shifter are integrally provided in one of the probe optical path and the reference optical path.

8. The phase shift interferometer according to claim 3, wherein the control unit comprises:
a first reception unit that receives the interference signal of the first light component;
a second reception unit that receives the interference signal of the second light component; and
a third reception unit that receives the interference signal of the third light component.

9. The phase shift interferometer according to claim 3, wherein the data acquisition unit acquires, as a measurement unit, the first light component, the second light component and the third light component as a data set in time series with each sweep of the wavelength.

10. The phase shift interferometer according to claim 1, wherein the sample measurement unit comprises:
a first internal path that includes one end connected to the fifth incidence and emission end and the other end connected to an incidence end of the sample that is the measurement target, the first internal path including a single mode optical fiber having a polarization-maintaining characteristic; and
a second internal path that includes one end connected to an emission end of the sample, and the other end having a total reflection minor provided therein, the second internal path including a single mode optical fiber having a polarization-maintaining characteristic.

11. The phase shift interferometer according to claim 1, wherein the sample measurement unit comprises:
an internal path that includes one end connected to the fifth incidence and emission end and the other end from which parallel light is emitted, the internal path including a single mode optical fiber having a polarization-maintaining characteristic; and
a lens that condenses the parallel light emitted from the other end of the internal path and radiates the resultant parallel light on the surface of the sample that is the measurement target, and wherein
reflected parallel light reflected from the surface of the sample and then incident from the other end of the internal path is emitted from the fifth incidence and emission end as the second reflected propagation light.

12. The phase shift interferometer according to claim 1, wherein the data acquisition unit converts the spectral phase acquired as a function of a wavelength to a function of a frequency, obtains a dispersion parameter from a spectral phase difference between adjacent frequencies, and obtains chromatic dispersion from the dispersion parameter.

13. The phase shift interferometer according to claim 11, wherein the data acquisition unit has an optical coherence tomography function of converting the spectral phase acquired as a function of a wavelength into a function of a frequency, performing an inverse Fourier transform of the spectral phase, and indicating an inverse Fourier transform of the spectral phase as a function of a propagation distance of the propagation light.

* * * * *